United States Patent [19]
Mordoh et al.

[11] Patent Number: 5,753,229
[45] Date of Patent: May 19, 1998

[54] MONOCLONAL ANTIBODIES REACTIVE WITH TUMOR PROLIFERATING CELLS

[76] Inventors: Jose Mordoh, Jose Hernandez 1837, Buenos Aires, Argentina, 1426; Silvia Leis De Cerone, Simbron 4304, Buenos Aires, Argentina, 1417; Osvaldo Luis Podhajcer, Ave. du General de Gaulle, Strasbourg, France; Alicia Ines Bravo, Sanabria 3287, Buenos Aires, Argentina, 1417

[21] Appl. No.: 335,573

[22] Filed: Nov. 7, 1994

Related U.S. Application Data

[63] Continuation-in-part of Ser. No. 285,545, Aug. 3, 1994, abandoned, which is a continuation of Ser. No. 185,752, Jan. 21, 1994, abandoned, which is a continuation of Ser. No. 766,862, Sep. 25, 1991, abandoned.

[51] Int. Cl.$^6$ .......................... A61K 39/395; C12N 5/10; C12N 5/12; C07K 16/30
[52] U.S. Cl. .......................... 424/155.1; 424/174.1; 435/344; 435/70.21; 435/172.1; 530/388.8; 530/387.1
[58] Field of Search .................. 435/70.21, 68.1, 435/172.1, 240.27, 344; 530/387.1, 388.8; 424/155.1, 174.1

[56] References Cited

PUBLICATIONS

Bellare C., Bravo A.I., Laucella S., Sorin I., Cerdeiro R., Loza J., Sousa Martinez F., Guman N. and Mordoh J. (1989): "DNA synthesis in estrogen receptor-positive human breast cancer takes place preferentially in estrogen receptor-negative cells". Cancer 64:842–848.

C. Ballare et al. (1993): "Marker Expression and Differentiation in Human Breast Cancer". Annals of the New York Academy of Sciences, vol. 698: 143–147.

J. Mordoh et al. (1994): "Description of a new monoclonal antibody, FC-2.15, reactive with human breast cancer and other human neoplasias". The International Journal of Biological Markers, vol. 9, No. 3, 125–134.

L. Bover et al. (1991): "Description of a new human breast cancer cell line, IIB–BR–G, established from a primary undifferentiated tumor". Breast Cancer Research and Treatment 19: 47–56.

J. Mordoh et al.: "Phase I Clinical Trial in Cancer Patients of a New Monoclonal Antibody FC–2.15 Reacting with Tumor Proliferating Cells". Journal of Immunotherapy 17:151–160, 1995.

O. Podhajcer et al. (1988): "Effect of Estradiol and Tamoxifen on the Anchorage–Independent Growth of the Subpopulations Derived from MCF–7 Breast Carcinoma Cells: Cytogenetic Analysis of the Stem Cell Subpopulation". Experimental Cell Research 179: 58–64.

L. Reichmann et al.(1988): "Reshaping human antibodies for therapy". Nature 332:323–327.

C. Arteaga et al. (1989): "Growth Inhibition of Human Breast Cancer Cells in Vitro with an Antibody against the Type I Somatomedin Receptor". Cancer Research 49:6237–6241.

Z. Ronai et al. (1986) "(Auto)antibodies in Human Breast Cancer Sera Against Antigens Associated with Breast Cancer Cells, Detected by Immunoblotting". JNCI 77:1203–1209.

Current Protocols in Molecular Biology, "Immunology", Chapter 11, Supplement 1.

Sevier, E.D. et al, Clin Chem. 27(11):1797–1806, 1981.
Buick, R.N. et al, Cancer Research, 44:4909–4918, Nov. 1984.
Bravo, A.I. et al., J. Exp. Clin Can Res., 4(3):317–324, 1985.
Sorin, I. et al, J. Exp. Clin Can Res, 7(1):35–42, 1988.
Podhajcer, O.L. et al, Cancer, 58:720–729, 1986.
Galfré, G. et al, Meth Engymol, 73(part B):3–46, 1981.
Resnicoff, M. et al, PNAS, 84:7295–7299, Oct. 1987.
Hamburger, A. W. et al, Science, 197:461–463, 1977.
Guerra, L. et al, Pigment Cell Res, 2:504–509, 1989.
Fraker, P.J. et al, Biochem. Biophys. Res. Commun, 80(4):849–857, Feb. 28, 1978.

*Primary Examiner*—Susan A. Loring
*Attorney, Agent, or Firm*—Darby & Darby

[57] ABSTRACT

This invention concerns monoclonal antibodies directed against breast carcinoma cells. Immunoglobulin secreting hybridoma cultures are produced by hybridoma technology using undifferentiated breast cancer cells as antigens for immunization. Hybridomas secreting antibodies highly reactive with tumor proliferating cells are selected. These monoclonal antibodies have particular application in aiding the diagnosis or treatment of cancer.

7 Claims, 15 Drawing Sheets

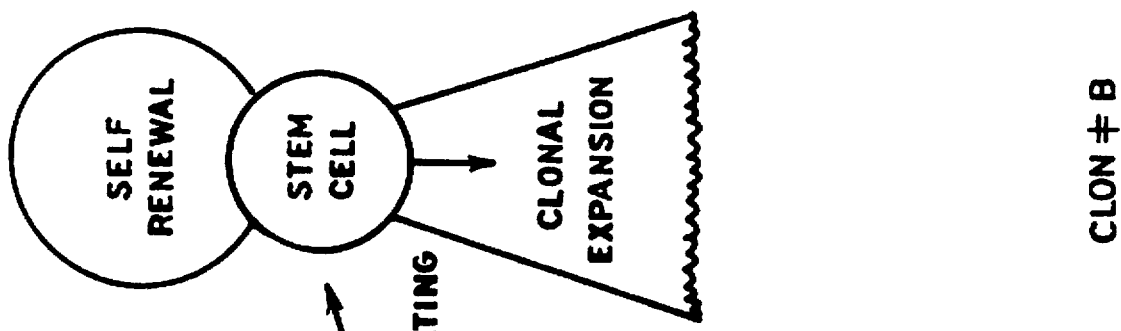
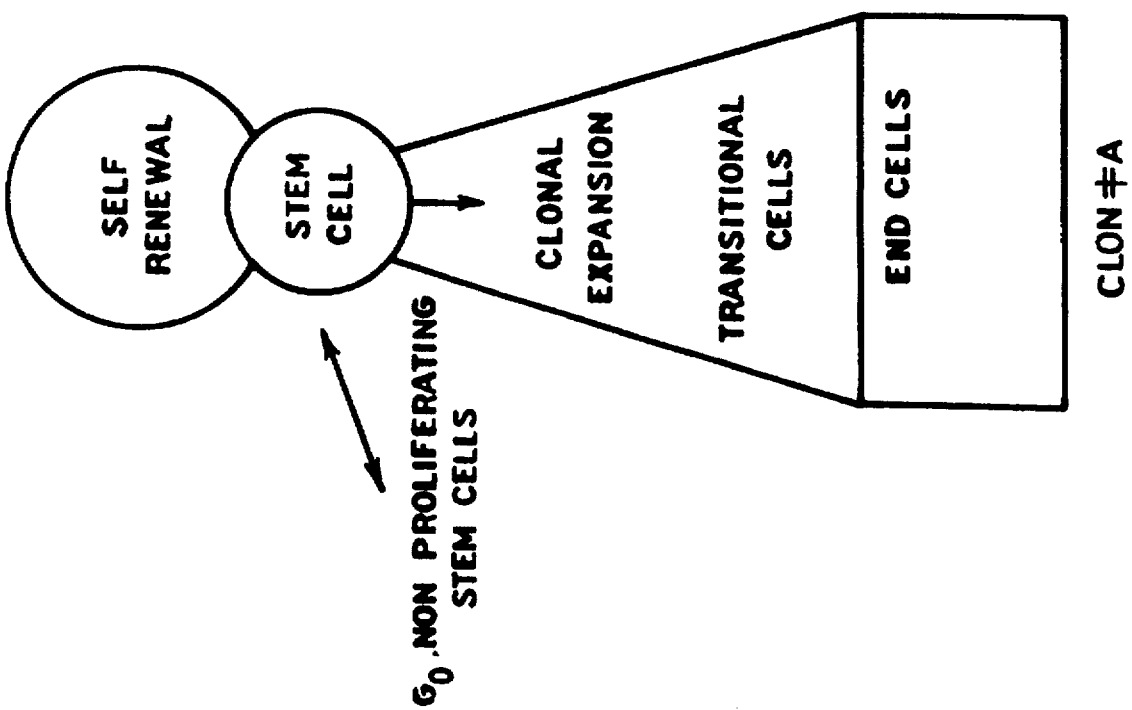
FIG. 1

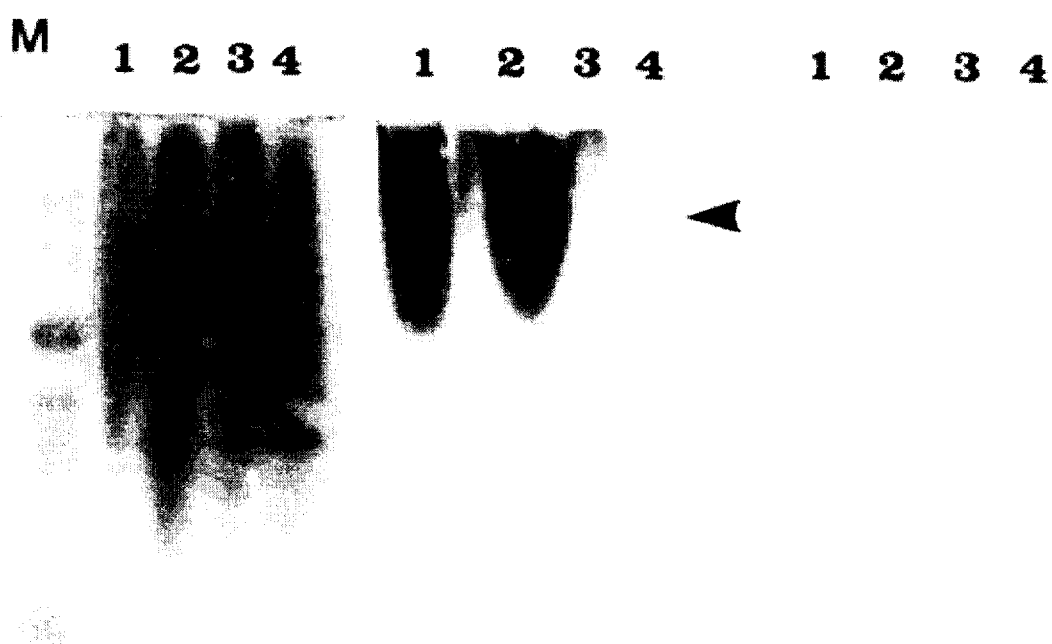

FIG. 10A
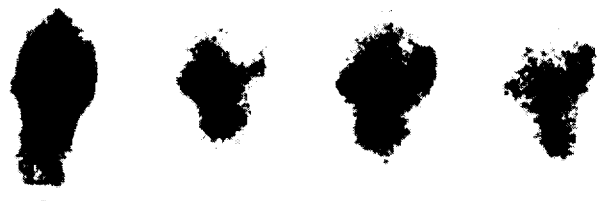
FIG. 10B

V region of heavy chain:

```
1  AG GTG AAG CTG CAG GAG TCT GGA GGT GGC CTC GTG CAG CCT GGA
      val lys leu gln glu ser gly gly gly leu val gln pro gly GGA TCC CTG AAA CTC TCC TGT GCA GCC TCA GGA TTC GAT TTT
   gly ser leu lys leu ser cys ala ala ser gly phe asp phe AGT AGA TAC TGG ATC AGT TGG CTC CGG CAG GCT CCA GGG AAA
   ser arg tyr trp met ser trp val arg gln ala pro gly lys GGG CTA GAA TGG ATT GGA GAA ATT AAT CCA GAT ACC AGT ACC
   gly leu glu trp ile gly glu ile asn pro asp ser ser thr ATA AAC TAT ACG CCA TCT CTA AAG GAT AAA TTC ATC ATC TCC
   ile asn tyr thr pro ser leu lys asp lys phe ile ile ser AGA GAC AAC GCC AAA AAT ACG CTG TAC CTG CAA ATG AGC AAA
   arg asp asn ala lys asn thr leu tyr leu gln met ser lys GTG AGA TCT GAG GAC ACA GCC CTT TAT TAC TGT GCA AGA GAG
   val arg ser glu asp thr ala leu tyr tyr cys ala arg glu ACT GGG ACG CCT TTT GAC TAC TGG GGC CAA GGC ACC ACT CTC
   thr gly thr pro phe asp tyr trp gly gln gly thr thr leu ACA GTC TCC TCA GAG AGT CAG TCC TTC CCA AAT  -361
   thr val ser ser glu ser gln ser phe pro
```

FIG. 13B

V region of light chain:

```
1   GAT ATT GTG ATG ACC CAG TCT CCA GCA TCC CTG TCC GTG GCT
    asp ile val met thr gln ser pro ala ser leu ser val ala ACA GGA GAA AAA GTC ACT ATC AGA TGC ATA ACC AGC ACT GAT
    thr gly glu lys val thr ile arg cys ile thr ser thr asp ATT GAT GAT ATG AAC TGG TAC CAG CAG AAG CCA GGG GAA
    ile asp asp met asn trp tyr gln gln lys pro gly glu CCT CCT AAG CTC CTT ATT TCA GAA GGC AAT ACT CTT CGT CCT
    pro pro lys leu leu ile ser glu gly asn thr leu arg pro GGA GTC CCA TCC CGA TTC AGT GGC AGT GGC TAT GGC ACA GAT
    gly val pro ser arg phe ser ser gly ser gly tyr gly thr asp TTT GTT TTT ACA ATT GAA AAC ACG CAC TCA GAA GAT GTT GCA
    phe val phe thr ile glu asn thr his ser glu asp val ala GAT TAC TAC TGT TTG CAA AGT GAT AAC ATG CCA TTC ACG TTC
    asp tyr tyr cys leu gln ser asp asn met pro phe thr phe GGC TCG GGG ACA AAG TTG GAA ATA AAA CGG GCT GAT GCT GCA
    gly ser gly thr lys leu glu ile lys arg ala asp ala ala CCA ACT GTA TCC A- 349
    pro thr val ser
```

MONOCLONAL ANTIBODIES REACTIVE WITH TUMOR PROLIFERATING CELLS

This application is a continuation-in-part of Ser. No. 08/285,545, filed Aug. 3, 1994, now abandoned, which is a continuation of Ser. No. 08/185,752, filed Jan. 21, 1994, now abandoned, which is a continuation of Ser. No. 766,862 filed Sep. 25, 1991 now abandoned.

FIELD OF THE INVENTION

This invention pertains to monoclonal antibodies and their use in the diagnosis or treatment of cancer.

BACKGROUND OF THE INVENTION

One of the most notable aspects of human neoplasia is the high degree of cellular heterogeneity observed. In recent years the "Hypothesis of cellular hierarchy" has been investigated (Buick, R. R. and Pollack, M. N., (1984), "Perspectives on clonogenic tumor cells, stem cells and oncogenes". Cancer Res. 44:4909–4918). Essentially, this hypothesis proposes that rapidly proliferating normal tissues (bone marrow, intestine) and tumors, contain three categories of cellular populations:

1) Stem cells, responsible for tissue proliferation and for originating a differentiated cell progeny and, in the case of tumors, also for the generation of the metastasis;

2) Transitional cells, which retain a limited proliferating ability and begin to acquire certain differentiation characteristics; and 3) Differentiated or terminal cells, which have lost the capacity to proliferate and have achieved the maximum degree of differentiation of which normal tissues or a specific tumor is capable. Variation in differentiation levels is thus a source of cellular heterogeneity, since in normal tissues and in tumors it can be produced within the same clone, i.e., a group of cells arising from a single stem cell. Tumors may contain an additional source of heterogeneity due to the presence of different clones, arising as a consequence of multiple mutations, which may in turn achieve different levels of differentiation. FIG. 1 presents a schematic view of the coexistence in a tumor of different clones with diverse differentiation capacity.

The main difference in an adult organism between normal and tumor tissues is that in the former, stein cell division is governed in such a way as to compensate exactly for the cellular loss due to normal metabolism; therefore, the size of the total population remains constant. On the other hand, stem cell division in tumors is disrupted in such a way that the size of the total population (the tumor) expands progressively.

From the foregoing it is reasonable to assume that elimination of the different components of cellular hierarchy would have different effects on tumor evolution and clinical responses observed (FIG. 2). Elimination of stem cells would be the only viable method to cure a tumor, since such cells are the only ones capable of regenerating the tumor. If therapies applied fail to achieve the total elimination of stem cells, the tumor would regenerate from the remaining stem cells. Elimination of transitional and/or differentiated cells would determine clinical responses of varying significance because these cells frequently constitute the majority of tumor mass. Nevertheless, the tumor would inevitably recur if the stem cell group were not affected.

Different methods may be used to identify the various components of the cellular hierarchy (FIG. 3): 1) Human tumor stem cells, and part of transitional cells, may be identified by incorporation of ($^3$H)thymidine into DNA, a characteristic of cells engaged in cellular division; 2) stem cells may also be identified by their capacity to form colonies (i.e., groups of more than 30 cells) in clonogenic assays in soft-agar, and their capacity to generate tumors in nude mice; 3) Tumor antigens expressed by the different subpopulations may be recognized by specific antibodies. A detailed knowledge of the stem cells subpopulation, its biological characteristics and the antigens it expresses is a basic requisite for producing monoclonal antibodies with therapeutic or diagnostic potential with respect to malignant tumors.

Considerable evidence has accumulated with respect to the presence of cellular subpopulations in breast cancer. Prior work has investigated whether the expression of the tumor marker carcinoembryonic antigen (CEA) is associated with a particular tumor cell subpopulation. Results obtained in 114 patients revealed that CEA was expressed by the most differentiated breast tumors (Bravo, A. I., Sorin, I., Guman, N. and Mordoh, J., (1985), "Carcinoembryonic antigen and differentiation in human breast cancer". J. Exp. Clin. Cancer Res., 4:3–10). Since the degree of differentiation of a tumor is inversely proportional to the number of stem cells (FIG. 1), these results suggested that CEA was expressed by the differentiated cells and not by stem cells. Nevertheless, these results did not provide direct evidence that stem cells did not express CEA. Therefore, a technique for simultaneous detection in tissue samples of cells engaged in active DNA synthesis (estimated by ($^3$H) thymidine incorporation and autoradiography) and those expressing CEA (by immunohistochemistry) was developed. Using this technique, it was conclusively demonstrated that: a) proliferating cells, which include the stem cells subpopulation, constituted a minor fraction (<3%) of total tumor cells; b) stem cells did not express CEA, and c) CEA content was inversely proportional to the TLI (Thymidine labelling index), which reflects the number of cells in the S phase of the cell cycle (Sorin, I., Bravo, A. I., Podhajcer, O. L., Bover, L., Loza, J., Sousa Martinez, F., Guman, N. and Mordoh, J., (1988), "Analysis of DNA synthesis and carcinoembryonic antigen expression in human breast cancer". J. Exp. Clin. Cancer Res., 7:35–42). This work demonstrated that CEA is a marker of cell differentiation antigen not expressed by stem cells.

In order to further study the characteristics of stem cells in breast cancer, the expression of hormone receptors has been studied. It is known that approximately two thirds of breast cancer patients exhibit estrogen receptors (ER) and that approximately 60% of these patients respond to antihormone treatment vs. 5–10% of patients with ER- tumors (Jensen, E. V., (1975), "Estrogen receptors in hormone-dependent breast cancers". Cancer Res., 35:3362–3364). Nevertheless, antihormone therapy in breast cancer rarely constitutes a cure, since frequent recurrences of the disease occur. Therefore, an analysis was undertaken of ER expression in the differentiation pathway of mammary cancer cells to study whether stem cells express ER. The answer to this question was of great practical importance since antihormone therapy could constitute a cure only if stem cells express ER. On the other hand, if ER are only expressed by differentiated cells, their elimination may have palliative but not curative effect. This study was undertaken in primary tumors. It was observed that DNA-synthesizing cells did not express ER, thus demonstrating that ER expression is a product of cellular differentiation (Podhajcer, O. L., Bravo, A. I., Sorin, I., Guman, N., Cerdeiro, R. and Mordoh, J., (1986), "Determination of DNA synthesis, estrogen receptors and carcinoembryonic antigen in isolated cellular subpopulations of human breast cancer". *Cancer,* 58:720–729). More recent work has confirmed these observations, i.e., it was determined that in ER+ breast tumors, 70% of the cells in the S phase of the cell cycle do not express ER (Ballare, C., Bravo, A. I., Laucella, S., Sorin, I., Cerdeiro, R., Loza, J., Sousa Martinez, F., Guman, N. and Mordoh, J., (1989), "DNA synthesis in estrogen receptor-positive human breast cancer takes place preferentially in estrogen receptor-negative cells". *Cancer,* 64:842–848).

Further direct evidence with respect to the presence of stem cells in breast cancer emerged from studies performed with the MCF-7 breast cancer cell line. Using Percoll gradient centrifugation, it was possible to separate different cellular subpopulations, one of which proved extremely rich in stem cells, its principal characteristics being a high growth rate and the capacity to regenerate the other subpopulations (Resnicoff, M., Medrano, E. E., Podhajcer, O. L., Bravo, A. I., Bover, L. and Mordoh, J., (1987), "MCF-7 cells separated by Percoll gradient centrifugation : a model to analyze the heterogeneity of human breast cancer". *Proc. Natl. Acad. Sci. (USA),* 84:7295-7299).

Thus, it has been demonstrated that within breast tumors there is a high degree of cellular heterogeneity, which is due, among other factors, to the coexistence of a highly proliferative stem cell subpopulation with more differentiated cells. It is therefore important to eliminate stem cells to cure a tumor.

Although monoclonal antibodies recognizing tumor-associated antigens have been produced in the past, they have not been directed against the proliferative subpopulation of tumors. This may explain the lack of therapeutic success using those antibodies. A diagnostic and therapeutic need, therefore, exists for monoclonal antibodies directed against tumor proliferating cells.

SUMMARY OF THE INVENTION

This invention relates to a method for producing monoclonal antibodies directed against proliferative cells of human breast carcinomas. Mice are immunized with undifferentiated breast carcinoma cells. Splenic lymphocytes of the immunized mice are then fused with a cell line. A clonal line of hybrid cells which produces antibodies which are reactive with breast carcinoma proliferative cells is then selected and grown. The clonal cell line should preferably be screened to detect secreted antibodies that possess one or all of the following properties:

A. inhibition of colony forming capacity of breast carcinoma cell lines and breast primary and metastatic carcinomas;

B. reactivity with primary and metastatic breast carcinomas;

C. reactivity with neoplasia of diverse origin, preferably melanoma, prostate carcinoma, colon carcinoma, and thyroid carcinoma; or D. lack of reactivity with normal cells of lymph nodes, liver, ovary and brain, mild positive reactivity with endometrium and epidermis, and strong reactivity with pancreas, kidney, bone marrow myeloid progeny cells and peripheral granulocytes.

Most preferably, antibodies produced by the clonal cell line have the capacity to induce regression of metastatic human carcinomas in cancer patients, induce aggregation of human peripheral granulocytes in vitro and their depletion from circulation in vivo, or the ability to detect human tumors growing in immunodeficient mice when bound to radiochemicals.

The invention also relates to antibodies produced by cell lines obtained by these methods, to the cell lines themselves, and to a method of administering these antibodies to an individual. The invention also relates to an improved method for determining the presence of cancerous cells wherein a monoclonal antibody specific for the cancerous cells is reacted with the cells and the presence of the monoclonal antibody is detected. The improvement is the use of a specified monoclonal antibody.

BRIEF DESCRIPTION OF DRAWINGS AND FIGURES

FIG. 1 is a schematic diagram of cellular hierarchy in tumors, in which the coexistence of clones with diverse differentiation capacities is shown.

FIG. 4 shows strong positive immunoreactivity of monoclonal antibody FC-2. 15 with different human tumors after performing immunohistochemical detection at a magnification of 400×. FIG. 4A shows a human breast carcinoma. FIG. 4B shows a human breast carcinoma with predominant membrane staining (arrow). FIG. 4C shows an epidermoid squamous carcinoma. FIG. 4D shows a colon carcinoma (D).

Figure 5A:
Figure 5B:

FIG. 5 is a photograph (400×) showing the reactivity of different antibodies with breast carcinoma proliferating cells. Several primary breast carcinomas were incubated with ($^3$H) thymidine. Afterwards, immunohistochemical detection was performed with monoclonal antibody anti-CEA (A) and monoclonal antibody FC-2.15 (B), followed by autoradiography. Silver grains are observed on DNA-synthesizing cells (arrows). In FIG. 5A proliferating cells do not express CEA (arrow). In FIG. 5B every proliferating cell is detected with FC-2.15 (arrows).

Figure 6A:
Figure 6B:
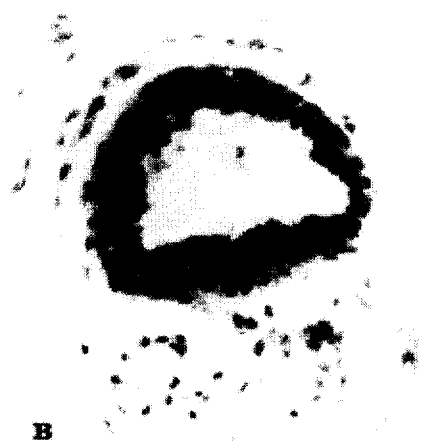
Figure 6C:
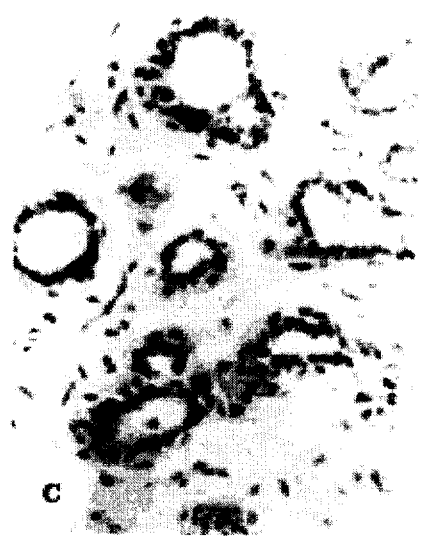

FIG. 6 shows FC-2.15 reactivity with benign breast pathologies and normal breast (400×). FIG. 6A shows a breast adenosis with low reactivity. FIG. 6B shows a breast hyperplasia with strong reactivity. FIG. 6C shows a normal breast with no reactivity.

Figure 7:
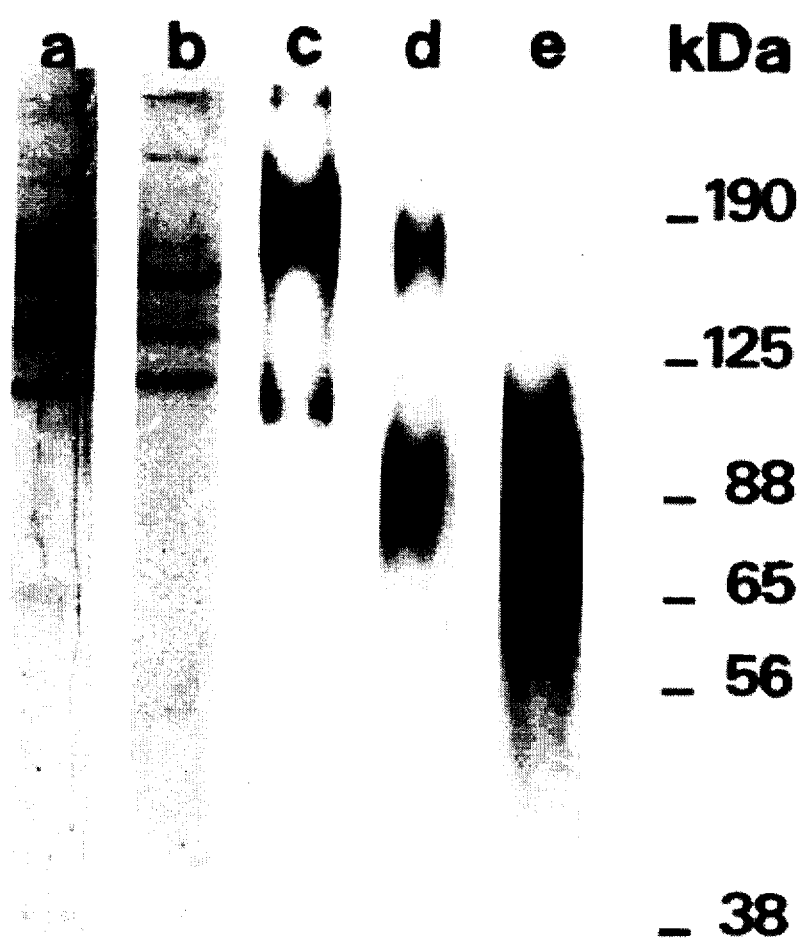

FIG. 7 shows a Western blot analysis of MAb FC-2. 15 reactivity. Membrane extracts were analyzed by Western blots. Lane (a): MCF-7 cells; Lane (b): breast primary tumor. Only one tumor is shown; another tumor revealed an identical pattern; Lanes (c), (d) and (e): peripheral granulocytes. The primary antibody used in lanes (a), (b) and (c) was FC-2. 15; in lane (d) it was B1.1 and in lane (e) B6.2. Molecular weight markers are indicated on the right.

FIG. 8 shows a western blot analysis of MAb FC-5.01 reactivity. 150 ug of melanoma proteins extracts were loaded on each lane of a native 7.5% polyacrylamide gel. After transfer into nitrocellulose, total protein were stained with Coomassie Brillant Blue (A). Transferred proteins were also treated with MAb FC-5.01 (B) and PBS (C), and developed. Membrane samples were extracted with 1% NP-40 (1), 1% SDS (2) and 1% Triton X-114 (3). Lane 4 corresponds to the cytosol.

FIG. 9 shows the effect of FC-2.15 on in vitro agglutination of normal peripheral granulocytes and on the formation of mixed clumps between granulocytes and tumor cells expressing antigen FC-2.15. FIG. 9A shows granulocytes incubated in vitro with FC-2.15 (50 ug/ml). FIG. 9B shows mixed clumps formed incubating granulocytes with MCF-7 cells (positive with FC-2.15) (10:1) in the presence of FC-2.15 (50 ug/ml). FIG. 9C shows incubation of granulocytes with IIB-BR-G cells (negative with FC-2.15) (10:1) in the presence of FC-2.15 (50 ug/ml). Absence of mixed clumps is observed. FIG. 9D shows, by phase contrast microscopy, incubation of granulocytes with IIB-MEL-J cells (negative with FC-2.15) (10:1) and FC-2.15 (50 ug/ml). Absence of mixed clumps is observed. T=tumor cells; G =granulocytes. Original magnification : 400×.

FIG. 10 shows the immunodetection of human IIB-BR-G tumors using radiolabeled MAb FC-5.01. Balb/c nu/nu mice bearing contralateral tumors were i.p. injected with 300 uCi of $^{125}$I-FC-5.01 (A) or $^{125}$I-UPC10 (Sigma Chemical Co.) (B). Scintiphots were taken for several days after injection.

Figure 11A:
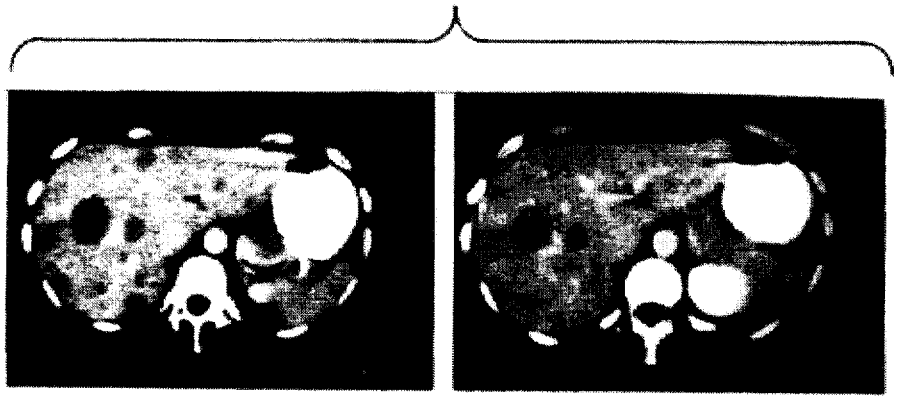
Figure 11B:
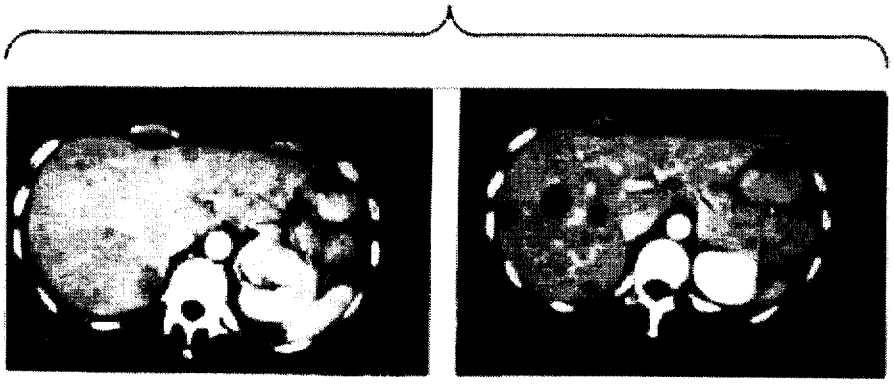
Figure 11C:

FIG. 11 shows computarized axial tomographies (CAT scans) of a patient (ASR) with advanced breast carcinoma, treated with 98 mg (2.5 mg/kg) of MAb FC-2.15. For each date, two different CAT sections are shown. The images of Dec. 16th, 1992 demonstrate the presence of liver metastases at the beginning of treatment (Jan. 4th, 1993). The images of Feb. 2nd, 1993 (29 days after the start of treatment), demonstrate a considerable diminution in the size and number of hepatic metastases. This improvement is even more remarkable 106 days after starting treatment (Apr. 20th, 1993).

Figure 12A:
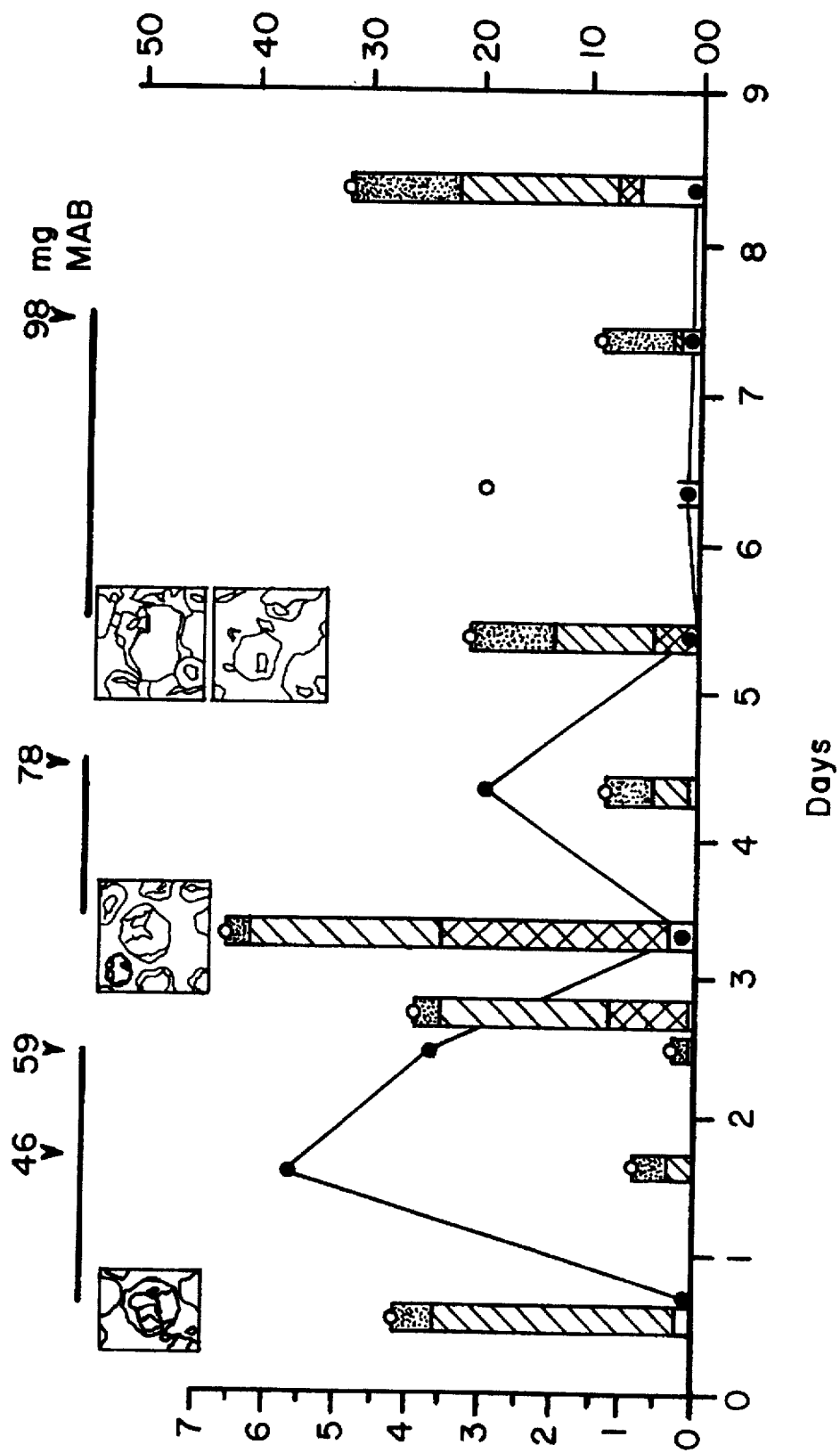
Figure 12B:
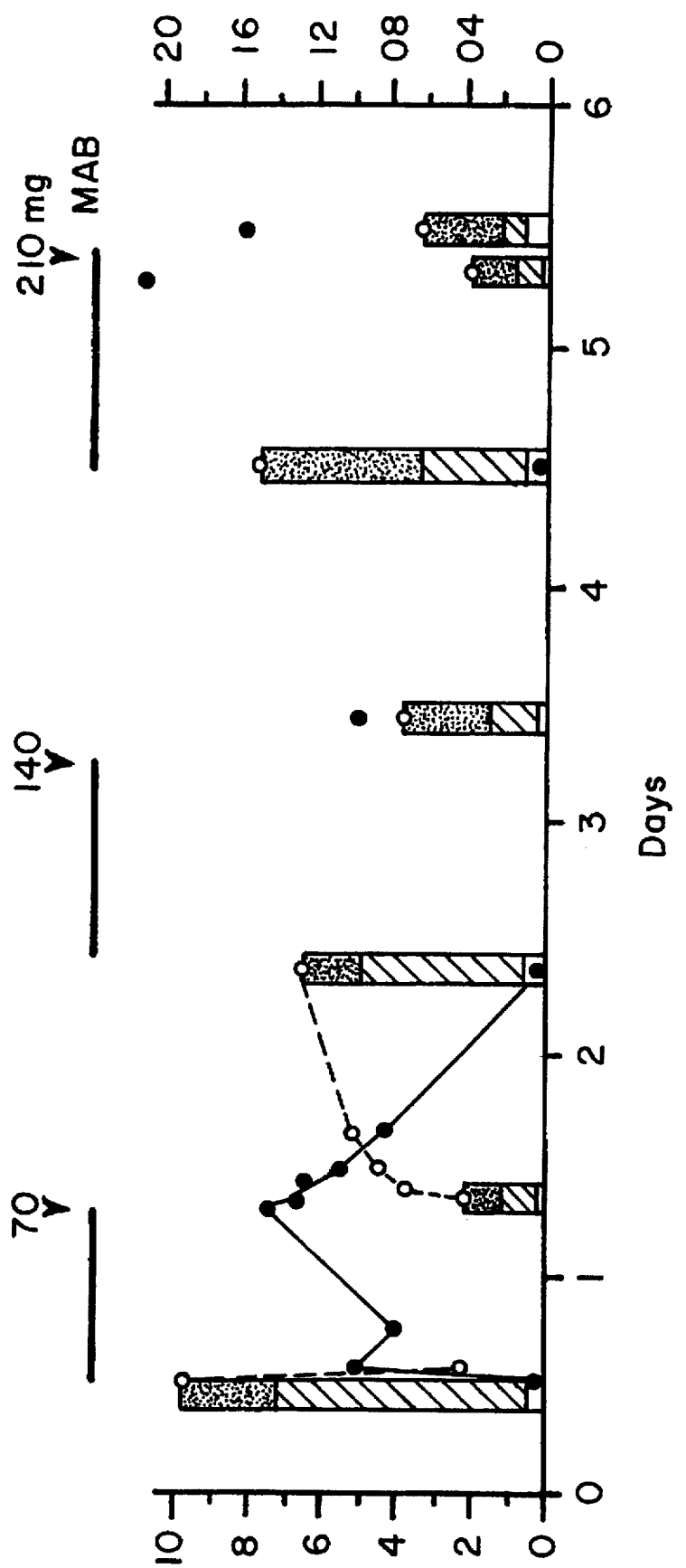

FIG. 12 shows the evolution of MAb FC-2.15 blood levels (−) and of white blood cells (WBC) (o—o) during the treatment of two patients (ASR and HDF) with MAb FC-2.15. The serum concentration of FC-2.15 was determined (−) and the number of total WBC (vertical bars), lymphocytes (dotted bars), segmented granulocytes (black bars), juvenile (horseshoe shaped) granulocytes (hatched bars) and monocytes (white bars) were determined in blood. In the photographs some circulating WBC at the indicated times are shown. Horizontal bars indicate the application period of the MAb and its cumulative doses.

FIG. 13 shows the nucleotide and amino acid sequence of FC-2.15 heavy and light chain V regions. The sequence corresponding to the oligonucleotide primers is indicated.

DETAILED DESCRIPTION OF THE INVENTION

Although specific reference to human breast cancer is made below, the monoclonal antibodies described herein (and the corresponding hybridoma cell lines), whose target are the proliferating cells of breast cancer, may be reactive with other targets, such as prostate cancer, colon cancer and melanomas.

We specifically describe herein the derivation of two monoclonal antibodies (MAb) FC-2.15 and FC-5.01 directed against human breast cancer stem cells, which are the tumor subpopulation responsible for tumor development and dissemination. These monoclonal antibodies may be used in the detection or treatment of breast cancer. We used cells isolated from human breast cancer undifferentiated tumors as immunogen to isolate the MAb named FC- 2.15. All the hybridoma supernatants obtained in this fusion also reacted with peripheral granulocytes (see below). Further immunizations were performed using as immunogen, cells isolated from an undifferentiated human breast cancer cell line, IIB-BR-G (Bover, L., Barrio, M., Slavutsky, I., Bravo, A. L, Quintans, C., Bagnati, A., Lema, B., Schiaffi, J., Yomha, R. and Mordoh, J., (1991), "Description of a new human breast cancer cell line IIB-BR-G, established from a primary undifferentiated tumor". *Breast Cancer Research and Treatment*, 19:47–56). In this case, hybridoma supernatants were also selected by their negative reactivity with human blood cells and bone marrow cells. By using this approach a second MAb was selected, and named FC-5.01. Spleens isolated from immunized Balb-C mice were fused with NSO/1 or X63-Ag8.653 murine myeloma cells and a total of 111 hybridoma primary cultures were obtained. An immunocytochemical approach was used to determine the reactivity of the different hybridoma supernatants with the cells used as immunogens. The two hybridomas FC-2.15 and FC-5.01 were selected after: a) two selections by end-point dilution, b) testing the reactivity of the hybridoma supernatants with normal, benign and malignant human tissues and isolated cells, and in some cases c) testing their ability to reduce the clonogenic capacity of tumor cells without affecting bone marrow cells clonogenic capacity. Both MAbs react with primary and metastatic human mammary carcinomas. In addition, at least one of them also reacts with human malignant melanomas, thyroid carcinomas, colon carcinomas, lung carcinomas, prostate carcinomas, squamous carcinomas of skin and larynx, clear cell renal carcinomas and pancreatic adenocarcinoma.

The MAbs described in this application can be used in conventional detection methodologies for cancer. They are also useful in human breast cancer treatment, as they react with proliferating tumor cells. As shown below, we have demonstrated the regression of visceral metastasis in one breast cancer patient after treatment with MAb FC-2.15. The hybridoma cell line producing MAb FC-2.15 was deposited on Jun. 1, 1994 with the Acociacion Banco Argentino de Celulas, Av Patricias Argentinas 435, 1405, Buenos Aires, Argentina and accorded deposit number FC-215. The hybridoma cell line producing MAb FC-215 was deposit on Jun. 12, 1997 with the Collection Nationale de Cultures de microorganisms, Institute Pasteur, 25, Rue du Docteur Roux, 75724 Paris Cedex 15, France and accorded deposit number I-1875. MAb FC-5.01 has particular use for tumor localization using immunoscintigraphy. The hybridoma cell line producing mab FC-5.01 was deposited on Jun. 1, 1994 with the Acociacion Banco Argentino de Celulas (ABAC), I.N.E.V.H., CC. 195, 2700 Pergamino, Argentina and accorded deposit number FC-5.01. The hybridoma cell line producing MAb FC-5.01 was deposited on Jun. 12, 1997 with the Collection Nationale de Cultures de Microorganisms, Institute Pasteur, 25, Rue du Doceteur Roux, 75724 Paris Cedex 15, France and accorded deposit number I-1876.

EXAMPLES

1) Preparation of cells for mice immunization

A) Isolation of cells from a human undifferentiated breast carcinoma

Two gr of a highly undifferentiated human primary breast carcinoma, negative for estrogen and progesterone receptors, was trimmed from fat and normal surrounding tissues, cut into small pieces and resuspended in 6 ml of Eagle's Minimum Essential Medium (Gibco Laboratories, Madison, USA) containing penicillin (100 U/ml), streptomycin (100 ug/ml), 10% heat inactivated (30 min. at 56° C.) fetal bovine serum (FBS) (Flow) and the following enzymes: 1 mg/ml Type I collagenase (Sigma); 1 mg/ml Type IS hyaluronidase (Sigma); 0.2 mg/ml DNAse I (Sigma) and 0.1 mg/ml Type I elastase (Sigma). The tissue suspension was kept for 4 hr at 37° C. with gentle mechanical agitation. The resulting cellular suspension was filtered through gauze and subsequently washed with 2 ml of fresh sterile medium. The filtrate containing the isolated cells was decanted over 30 min. at 37° C. on a plastic Petri dish, and non-adherent cells ($25\times10^6$ in 15 ml) were layered on a Ficoll (Type 400, Sigma )—Hypaque (Whintrop Products, New York, USA) gradient (7.2 ml 8% Ficoll+3 ml 33% Hypaque). After centrifugation at 2,500 rpm for 30 min., the interphase containing the tumor cells was separated and diluted with phosphate buffered saline (PBS) and the cells were counted. Seventeen million cells were recovered and frozen in liquid nitrogen at a concentration of $10\times10^6$ cells/ml of the following medium: 70% MEM - 20% FBS - 10% dimethylsulfoxide (Merck Darmstadt) in vials containing $2\times10^6$ cells per vial.

B) IIB-BR-G human breast cancer cells

Cells were grown at 37° C. in a 5% $CO_2$ atmosphere, in a 1:1 mixture of Dulbecco Minimal Essential Medium and F12 supplemented with 10% bovine fetal serum as indicated (see above Bover L. et at. (1991), ibid).

2) Immunization

A) Cells obtained from the primary tumor

Eight-weeks old Balb/c mice were immunized via intraperitoneal route with four separate injections at intervals of two weeks. The first injection contained $2\times10^6$ tumor cells and the three remaining injections contained $1\times10^6$ cells each. Three days after the final injection the spleen was removed under sterile conditions and splenocytes were extracted following Galfre and Milstein (Galfre, G. and Milstein, C., (1981), "Preparation of monoclonal antibodies: strategies and procedures". Meth. in Enzymol., Vol.73, part B:3–46).

B) IIB-BR-G cells

Eight-weeks old Balb-C mice were immunized via intraperitoneal route with 6 injections of IIB-BR-G cells every 21 days. Mice were alternatively immunized with $1\times10^6$ cells obtained as described before and $1\times10^6$ cells which were previously treated with 2% paraformaldehyde buffered with PBS. Four days before the mice were sacrificed, they were boosted with $20\times10^6$ unfixed cells. The spleen was removed and the splenocytes were obtained as previously described.

3) Fusion methodology

NSO mouse myeloma cells were used in the fusion step when the immunogen was the cell obtained from the primary breast carcinoma. NSO cells are derived from the mouse myeloma NS.1/1 Ag.4.1 and, unlike the latter, do not produce intracellular kappa light chains. Cell fusion was performed following the procedure described in Galfre and Milstein (see above Galfre, G. and Milstein, C., (1981), ibid).

When IIB-BR-G cells were used as the immunogen, X63-Ag8.653 mouse myeloma cells, which do not produce heavy and light Ig chains (Kearny, J. F., Radbruch, A., Liesegang, B., and Rajewsky, K., (1979), "A new mouse myeloma cell line that has lost immunoglobulin expression but permits the construction of antibody-secreting hybrid cell lines". J. Immunol., 132:1548–1550), were used in the fusion step. Cell fusion followed Galfre and Milstein (Galfre, G. and Milstein, C., (1981), ibid).

4) Cloning of hybridomas

The thymus was removed from a 6–8 week-old BALB/c mouse and transferred to a Petri dish. Thymocytes were removed by perfusion with 10 ml fusion cell culture medium, centrifuged for 5 min at 1,200 rpm and resuspended in 10 ml of the same medium. This procedure was repeated once more, and the thymocytes were resuspended at 20,000 cells/0.1 ml of HT 1×medium and distributed as feeder cells in 96-multiwell plates (Flow). For cloning, hybridoma cells were resuspended in HT 1×medium and 10 cells/well, 1 cell/well and 0.1 cell/well contained in 0.1 ml were added to each well previously seeded with thymocytes. After 10–15 days, the colony formation was examined under a microscope and the antibody reactivity of supernatants obtained from unique clones were analyzed. Clones with significant activity were transferred to 24-well plates and the cloning was repeated once more. Finally, one hybridoma cell line was selected after immunization with primary breast cancer cells and designated FC-2.15. A second hybridoma cell line designated FC-5.01, was selected from the fusions wherein the immunogen used was IIB-BR-G tumor cells. These hybridomas produce monoclonal antibodies of identical denomination.

5) Immunocytochemical assay

The following procedure was used to estimate the capacity of the different clones to produce antibodies against tumor cells. Tumor cells of the same origin as those which had been used for inoculation, and which were preserved in liquid nitrogen, were rapidly thawed at 37° C., diluted with Dulbecco-F12 1:1 culture medium (Gibco Laboratories, Madison USA), centrifuged at 1,000 rpm for 10 min. and resuspended in the same medium. When IIB-BR-G cells were used, nearly confluent cells were trypsinized, diluted in 10% FBS-containing medium, spun down in a table-top centrifuge for 5 min. at 1,000 rpm and resuspended in fresh medium without serum. Four ul containing 15,000 cells were added to each well on a "Multi-test" slide (Flow) to which 0.5 ul of 2% glutaraldehyde (Merck Darmstadt) had been previously added, and the slides dried in warm air. Subsequently, 10 ul of the supernatant from the different hybridomas were added and the slides were incubated overnight at 4° C. in a humid chamber. After 3 washings with PBS, 10 ul of a 1/1,000 dilution of rabbit anti-mouse immunoglobulin conjugated with horseradish peroxidase (Dakopatts, Denmark) were added. After 1 hr incubation at 37° C. the slides were washed 3 times with cold PBS, 5 min./wash. The reaction was developed by adding diaminobenzidine (DAB) (Sigma), 2 mg/10 ml of 0.05M Tris-HCI buffer (pH 7.6) and 0.03% $H_2O_2$. After 15 min. at room temperature in the dark, the slides were thoroughly washed with distilled water, and dried and stained with Harris hematoxylin for 20 sec. After washing with tap water, they were dried and observed under microscope. A positive reaction was detected as a dark brown precipitate formed in the place where the antigen-antibody contact occurred.

6) Immunohistochemical assay

Tissues were fixed in 3.7% formaldehyde dissolved in PBS. After normal processing, sections were cut from paraffin blocks and mounted on gelatinized slides. Endogenous peroxidase was blocked by incubating for 30 min. at room temperature in 2% $H_2O_2$ in methanol. To reduce non-specific background, tissue sections were blocked for 40 min at room temperature with 10% normal rabbit serum. Thereafter, slides were incubated with monoclonal antibody (undiluted hybridoma supernatant; 1/100 ascites or 50 ug/ml purified) overnight at 4° C. Subsequently, HRP-conjugated rabbit-anti-mouse immunoglobulin antibody (Dakopatts) was added for 90 min. at room temperature (dilution 1/50). The reaction was developed with DAB as indicated in the preceding Section. After each step, slides were washed 3 times with cold PBS, 5 min/wash. The slides were counterstained with Harris hematoxylin, dehydrated and mounted in Canada balsam.

7) Simultaneous determination of DNA synthesis and reactivity to monoclonal antibodies This was performed in accordance with published guidelines (see above Ballare C. et al., (1989), ibid). Primary breast tumors were obtained from lumpectomies or mastectomies performed on patients without prior treatment. The tumor tissue was cleansed of fat and normal surrounding tissue and the tumor was cut with a scalpel in small pieces of approximately 1 mm$^3$. These pieces were incubated for 1 hr. at 37° C. in Eagle's Minimal Essential Medium containing 10% FBS and 2 uCi/ml ($^3$H)thymidine (sp. act. 50–80 Ci/mmol, New England Nuclear, USA). At the end of the incubation period the tumor pieces were washed three times with cold PBS, 15 min/wash and fixed with 3.7% formaldehyde as indicated above. After tissue processing, immunohistochemical assays were performed as indicated above on paraffin-embedded tissues with the different monoclonal antibodies. The slides were washed 3 times with 5% trichloroacetic acid, 15 min/wash, twice with distilled water, 10 min/wash, dried at room temperature and processed in a dark room. The slides were dipped at 45° C. in Kodak NTB2 emulsion (Eastman Kodak) diluted 1:1 in 1% glycerol in bidistilled water. The slides were dried at 28° C. for 1 hr and exposed in the dark for two weeks at 4° C. The slides were developed with Kodak D19 developer (Eastman Kodak), dehydrated and mounted in Canada balsam. The peripheral areas of the tissue fragments were examined to detect cells with silver grains on the nucleus, which indicated DNA synthesis. At the same time, reactivity with the monoclonal antibodies was examined.

8) Cell lines

The following human breast cancer cell lines were used: the estrogen-receptor (ER) and progesterone-receptor (PR) positive MCF-7 cell line (Soule, H. D., Vazquez, J., Long, A., Albert, S. and Brennan, M., (1973), "A human cell line from a pleural effusion derived from a breast carcinoma". *J. Natl. Cancer Inst.*, 51:1409–15) and T-47D cell line (Keydar, I., Chen, L., Karby, S., et al., (1979), "Establishment and characterization of a cell line of human breast carcinoma origin". *Eur. J. Cancer,* 15:659–70); the ER-negative, PR-negative MDA-MB-231 cell line (Cailleau, R., Young, R., Olive, M. and Reeves, W. J., (1974), "Breast tumor cell lines from pleural effusions". *J Natl Cancer Inst,* 53:661–74) and the IIB-BR-G cell line (Bover, L., et al. (1991), ibid). In addition, the human melanoma cell line IIB-MEL-J was also used (Guerra, L., Mordoh, J., Slavutsky, I., Larripa, I. and Medrano, E. E., (1989), "Characterization of IIB-MEL-J: a new and highly heterogeneous human melanoma cell line". *Pigment Cell Res.,* 2:504–9). These cell lines were grown as indicated in the above cited references.

9) Study of complement cytotoxicity mediated by antibodies

A) Human breast cancer cell lines

MCF-7 human breast cancer cells were plated in 25 cm$^2$ flask (Corning) at a density of 300,000 cells/ml in Dulbecco's modified Eagle medium—HAM F12 (1:1) containing 2 mM glutamine, 100 U/mil penicillin, 100 ug/ml streptomycin, 10 ug/ml insulin and 10% FBS. After incubating at 37° C. in humid atmosphere (air: $CO_2$ 95%:5%), exponentially growing cells were detached by incubating for 10 min. at 37° C. with 5 ml 10% EDTA. After two washings with PBS, 300,000 cells were resuspended in 30 ul of monoclonal antibody (hybridoma supernatant) and incubated for 1 hr at 4° C. After that, 3 ul of rabbit complement (C') (Gibco) previously adsorbed for 1 hr in ice with an equal volume of AB human erythrocytes were added. The cells were incubated with C' for 1 hr at 37° C. and washed twice with PBS. Residual clonogenic capacity of the cells was determined in triplicate using the method of colony-formation in semisolid medium as indicated below. Controls were performed by incubating the cells only with C'.

B) Breast tumor cells isolated from primary tumors or metastatic axillary nodes.

Tumor cells isolated from four human breast carcinomas (three primary tumors and one axillary node metastasis) by enzymatic dissociation were purified as indicated above. They were subsequently treated with monoclonal antibodies and C' as indicated above.

C) Human bone marrow cells.

Bone marrow samples were obtained by puncture aspiration of the sternum or illiac crest from non-neoplastic patients. Samples consisting of 3–6 ml taken in heparinized syringes were diluted in 3 volumes of Iscove's modified Dulbecco medium (Gibco). The cell suspension was subjected to a Ficoll-Hypaque gradient (density=1.077 g/ml) and centrifuged at 4,900 g for 30 min. The cell layer present at the interphase was collected, resuspended in the same medium, distributed in tubes ($2\times10^5$ cells/tube) and centrifuged at 250 g for 10 min. The bone marrow cells were then used for two different purposes, a) in an ELISA assay, for hybridoma selection leading to the obtention of MAb FC-5.01, and b) for clonogenic assays using monoclonal antibodies and C' as indicated above.

10) Assay of the formation of breast tumor cell colonies in semisolid medium

This assay was performed following published procedures with minor modifications (Podhajcer, O. L., Resnicoff, M., Bover, L., Medrano, E. E., Slavutsky, I., Larripa, I. and Mordoh, J., (1988), "Effect of estradiol and tamoxifen on the anchorage-independent growth of the subpopulations derived from MCF-7 breast carcinoma cells: cytogenetic analysis of the stem cell subpopulation". *Exp. Cell Res.,* 179:58–64; Buick, R. N., and Fry, S. E., (1980), "A comparison of human tumor-cell clonogenicity in methylcellulose and agar culture". *Br. J. Cancer,* 42:933–936; Hamburger, A. W. and Salmon, S. E., (1977), "Primary Bioassay of human tumor stem cells", *Science,* 197:461–463). In general, 0.3 ml of 1% agar (Difco) dissolved in the corresponding culture medium was seeded onto 24 well plates and used as underlayer. $3\times10^5$ cells were incubated with antibody and C', washed with PBS and spun down for 5 min. at 1,500 rpm. Cells obtained from primary tumors were resuspended in 1 ml of 0.3% agar dissolved in the corresponding culture medium and layered on the agar base in triplicate (0.3 ml/well). In the case of cell lines, cells were resuspended in 3 ml of the corresponding culture medium, after which 0.1 ml of the cell suspension was mixed with 0.9 ml of 1.3% methylcellulose (Sigma) dissolved in culture medium and layered as above (0.3 ml/well). Colony formation was evaluated after 2–3 weeks incubation at 37° C. in humid atmosphere air: $CO_2$ (95%:5%). Aggregates of more than 30 cells were considered colonies. Control cells were treated with C' alone and the number of formed colonies was considered 100%.

11) Bone marrow cell colony formation assay

This assay was performed using a modification of a previously described method (Ash, R., Detrick, R. and Zanjani, E. D., (1981), "Studies of human pluripotential hemopoietic stem cells (CFU-GEMM) in vitro". *Blood,* 58:309–316). After treatment with monoclonal and C', 1–2×$10^5$ bone marrow cells were resuspended in 1 ml of a medium containing 0.9% methylcellulose, 30% FBS or plasma AB, 5% lymphocytes conditioned medium, $5\times10^{-5}$M beta-mercaptoethanol and erythropoyetin (1 U/ml), and seeded on P35 plates (Falcon). Following incubation for 14 days at 37° C. in a humid atmosphere air: $CO_2$ (95%:5%), the colonies formed were counted. Controls were treated with C' alone.

12) Production of monoclonal antibodies

Once stabilized, the clones were maintained in culture or were inoculated in Balb/c mice ($2\times10^6$ cells i.p./mouse), primed with 0.1 ml Pristane (Trade Mark) (2, 6, 10, 14-tetramethylpentadecane) (Aldrich) and irradiated (360 rads) 10 days previously. The resulting ascitic fluid was removed via paracenthesis, centrifuged at 1,500 rpm for 5 min. for clarification and frozen at -20° C. until purification. Only the batches with good activity at a 1/100 dilution determined by the ELISA (enzyme-linked immunosorbant assay) method were kept for further purification.

13) Monoclonal antibody purification method

A) IgM-producing hybridomas. The ascitic fluids were combined, centrifuged at 5,000 rpm for 20 min and precipitated with ammonium sulphate (30% saturation). After centrifuging at 10,000 rpm for 20 min., the supernatant was precipitated with ammonium sulphate (50% saturation), recentrifuged at the same speed, washed once with ammonium sulphate at the same concentration and resuspended in 1×PBS (¼th original volume). The suspension was dialyzed against 100 vol of 1×PBS and the dialyzate was centrifuged at 40,000 rpm for 1 hr. The supernatant (25 ml) was seeded on a 500 ml Sephacryl® S300 (Pharmacia) column and eluted with 1×PBS. Eighty fractions of 6 ml each were recovered. Absorbancy at 280 nm was measured, and aliquots were analyzed by polyacrylamide gel electrophoresis (Laemmli, U. K., (1970), "Cleavage of structural proteins during the assembly of the head bacteriophage T4". Nature (Lond). 227:680–5) to determine their composition. IgM-containing fractions were pooled. To inactivate possible viruses, the antibody solution was treated with 0.3% (final concentration) tri-n-butyl phosphate (TNBP) (Merck) for 4 hr. at 30° C. with gentle shaking. The suspension was dialyzed against 200 volumes of 1×PBS in apyrogen bidistilled water. To verify total dialysis of TNBP the following procedure was used: a) heparinized mouse blood was extracted; b) 50 ul of blood were incubated with: i) PBS; ii) TNBP-treated antibody before dialysis; iii) antibody after dialysis. After shaking, the tubes were centrifuged at 1,500 rpm for 10 min. In sample (ii) there was hemoglobin release into the supernatant. TNBP dialysis was considered to be satisfactory when the absorbancy of sample (iii) was equal to sample (i). After centrifuging at 10,000 rpm for 10 min the antibody preparation was filtered through 0.45 u Millipore filters. Protein concentration was determined by the Lowry's method (Lowry, O. H., Rosebrough, N. J., Farr, A. L. and Randall, E., (1951), "Protein measurement with the Folin phenol reagent". J. Biol. Chem., 193:265–75). Ten percent maltose was added to prevent IgM aggregation and the antibody was aliquoted in ampoules containing 20 mg protein (5 mg/ml). The activity of the antibody was measured against MCF-7 cells with an ELISA technique, and its sterility was determined by incubating an aliquot in Luria-Bertani medium during 4 days at 37° C. The purified antibodies were kept at -70° C.

B) IgG-producing hybridomas. In the case of IgG producing hybridoma cells, the ascitic fluids were pooled, centrifuged at 5,000 rpm for 20 min and the supernatant precipitated with ammonium sulphate at 50% (w/v) saturation. After centrifuging at 10,000 rpm for 20 min, the precipitates were washed once with 50% ammonium sulphate and recentrifuged at the same speed. They were then resuspended in PBS ($\frac{1}{10}$th the original volume) and dialyzed overnight against 200 volumes of 0.02M Tris-HCl buffer (pH 8.0) - 40 mM NaCl. The dialyzed material was mixed with an equivalent volume of 0.02M Tris-HCl (pH 8.0) and applied on a DEAE-Sephacel® (Pharmacia Fine Chemicals, Uppsala, Sweden) column, at 6 mg protein/ml resin. The column was washed with 2 volumes of 0.02M Tris-HCl (pH 8.0) - 20 mM NaCl and proteins were eluted with 10 volumes of a 20–300 mM NaCl linear gradient in 0.02M Tris-HCl (pH 8.0). Protein concentration was determined by absorption at 280 nm, and the protein composition of the different peaks was analyzed by polyacrylamide gel electrophoresis (see above Laemmli, U. K. et al, (1970), ibid). The tubes containing purified IgG, corresponding to the first eluted peak, were pooled, treated with TNBP as indicated above and dialyzed for 48 hr. against 200 vol of 1×PBS solution in pyrogen-free bidistilled water. The solution was centrifuged for 1 hr. at 40,000 rpm and the small precipitate was discarded. The supernatant was filtered through 0.22 um Millipore filters. The protein concentration of the ultrafiltrate was determined by Lowry's method, the antibody reactivity against MCF-7 cells by ELISA, and sterility by incubating an aliquot in Luria-Bertani medium for 4 days at 37° C. The monoclonal antibody solution was subsequently aliquoted and frozen at -70° C. until use.

14) ELISA (enzyme-linked-immunosorbent assay) method

MCF-7 cells in 0.1 ml culture medium were plated into 96 multiwell plates and grown overnight at 37° C. in a humid air-$CO_2$ (95%–5%) atmosphere. Blood cells derived from a Ficoll-Hypaque interphase (mostly mononuclear cells) and bone marrow cells were plated into multiwell plates and allowed to dry. Cells were washed once with PBS, fixed in 3.7% formaldehyde in PBS for 10–12 min. at room temperature, and washed 3 times with PBS for 5 min. each. A blocking step was performed with 1% bovine serum albumin (BSA) in PBS for 1 hr. at room temperature. Afterwards, the plates were incubated overnight at 4° C. with 100 ul of different dilutions of the monoclonal antibody. On the following day, the plates were washed three times, 5 min. each, with 1 mg/ml BSA and incubated with peroxidase-conjugated goat anti-mouse antibody for 90 min. at room temperature. After three washes with 0.1% BSA in PBS, 5 min. each, and two washes with 1×PBS, the plates were incubated with 100 ul o-phenylenediamine (1 mg/ml) in 0.1M citrate buffer (pH 4.5)+0.012% $H_2O_2$ for 15–30 min. in the dark at room temperature with constant shaking. The reaction was stopped with 100 ul of 8N sulphuric acid and the absorbancy was read at 415 nm in a Model 3550 Bio-Rad automatic microplate ELISA reader.

15) Monoclonal Antibodies isotyping

The isotypes of the different monoclonal antibodies were determined using radial immunodiffusion with specific antisera (Sigma). Monoclonal antibody FC-2.15 was found to belong to the IgM class and monoclonal antibody FC-5.01 to the IgG 2a class.

16) Immunofluorescence

MCF-7 cells were grown on round coverslips in the usual culture medium. After washing with PBS, the cells were fixed with 3.7% formaldehyde for 10 min. and washed again three times with PBS. A blocking step with 10% goat serum, 10 min., was performed. Hybridoma supernatant (50 ul) was then added and incubated at room temperature for 1 hr. After washing twice with PBS, 50 ul of a 1/50 dilution of fluoresceinated goat anti-mouse Ig (Cappel) was added and further incubated for 30 min at room temperature. After washing with PBS, distilled $H_2O$ and mounting, fluorescence was observed in a Zeiss microscope equipped with an epifluorescence attachment.

17) FC-2.15 antigen extraction and characterization

Different sources of antigen were used. MCF-7 cells were grown in female nude Balb/c mice (nu/nu, Comision Nacional de Energia Atomica, Argentina) supplemented with estradiol pellets (Innovative Research of America, Ohio, USA). Two human breast primary tumors were processed as previously indicated, and their positivity for FC-2.15 was determined by immunohistochemistry. For granulocytes isolation, 50 ml blood were mixed with 3 ml of 10% dextran (in 0.9% NaCl). After 1 hr. at room temperature, 15 ml of the supernatant were seeded on 10 ml of a 9% Ficoll - 33.9% Hypaque (24:10, v:v) gradient and centrifuged for 30 min. at 1,500 rpm. To lyse the remaining erythrocytes, the pellet was resuspended in 2 ml of lysis buffer (0.1M EDTA - 10 mM $KCO_3H$ - 0.155M $NH_4Cl$). After 10 min. at room temperature, 48 ml of PBS were added and centrifuged for 5 min. at 1,500 rpm. The pellet was essentially composed of granulocytes. One gr of breast tumor samples or $20 \times 10^7$ granulocytes was frozen in liquid N2, pulverized, resuspended in 2 ml of 10 mM Tris-HCl, pH 7.4- 1.5 mM EDTA - 0.5 mM DTT - 1 mM Phenyl Methyl Sulfonyl Fluoride (PMSF) and homogenized with a Polytron (2 series of 30 sec with a two-min. interval). The suspension was centrifuged for 10 min. at 1,000×g, 4° C., and the pellet washed with 1 ml of the same buffer. Both supernatants were combined and centrifuged at 100,000×g for 2 hr. The high-speed supernatant constitutes the "cytoplasmic extract". The 100,000×g pellet was solubilized for 15 min. at 4° C. with 1% NP40 in 50 mM Tris-HCl pH 8.0- 150 mM NaCl - 5 mM KCl - 5 mM MgCl2- 1 mM PMSF and constitutes the "membrane extract". The samples were loaded on a 7.5% SDS: polyacrylamide gel electrophoresis apparatus and transferred to nitrocellulose membranes (Schleicher and Schuell, 0.45 um). After blocking with 3% non-fatty milk in PBS for 1 hr. at room temperature, membranes were incubated overnight at 4° C. with the following monoclonal antibodies: FC-2.15 (50 ug/ml), B6.2 (Colcher, D., Horan Hand, P., Nuti, M. and Schlom, J., (1981), "A spectrum of monoclonal antibodies reactive with human mammary tumor cells". *Proc. Natl. Acad. Sci. (USA)*, 78:3199–203), 1/200 ascites or B1.1 (Colcher, D., Horan Hand, P., Nuti, M. and Schlom, J., (1983), "Differential binding to human mammary and non mammary tumors of monoclonal antibodies reactive with carcinoembryonic antigen". *Cancer Invest.*, 1:127–38), 1/200 ascites, washed three times with 0.05% Tween 20 in PBS, followed by 2 hr. incubation at room temperature with Fab2'-goat anti-mouse IgG and IgM conjugated with alkaline phosphatase (Jackson ImmunoResearch Laboratories, Inc.). After washing, bands were visualized with NBT-BCIP.

18) FC-5.01 antigen extraction and characterization

IIB-BR-G cells and breast cancer primary tumors were used as a source for antigen extraction and characterization. The procedure was essentially similar to that used for FC-2.15 antigen extraction with minor differences. FC-5.01 antigen was obtained after the membrane pellet was extracted either with 1% NP-40 or 1% SDS. "Membrane extracts" were loaded on SDS: polyacrylamide gels, electrophoresed and transferred onto nitrocellulose membranes. Western blots were developed as previously described for FC-2.15.

19) Periodate oxidation

A modification of previously described techniques was used (Magnani, J. L., Spitalnik, S. L., and Ginsburg, D., (1987), "Antibodies against cell surface carbohydrates: determination of antigen structure: *Meth. Enzymol*, 138:195–202). MCF-7 cells grown on round coverslips were fixed with 3.7% formaldehyde - 0.1% saponin in PBS and blocked with 1% BSA - 0.1% saponin in PBS. After washing with 0.05M sodium acetate buffer pH 4.5, coverslips were treated with 10 mM sodium periodate in the same buffer for 1 hr at room temperature in the dark and finally washed with 1% BSA - 0.1% saponin in PBS - 0.1% sodium azide (buffer A) for 30 min. After overnight incubation at 4° C. in a humid chamber with MAbs FC-2.15 (50 ug/ml) or MBrl (Menard, S., Tagliabue, E., Canevari, S., Fossati, G., Colnaghi, M. I., (1983), "Generation of monoclonal antibodies reacting with normal and cancer cells of human breast". *Cancer Res.*, 43:1295–300) (1/150 ascites) coverslips were washed with buffer A and further incubated for 2 hr. at room temperature with a 1/250 dilution of HRP rabbit anti-mouse Ig (Dako). After washing with buffer A, colour was developed in individual flat-bottom wells (Linbro) using 1 mg/ml o-phenylenediamine in 0.1M sodium citrate pH 4.5–0.012% $H_2O_2$ as substrate. After 15 min. the reaction was stopped with 8N $SO_4H_2$ and readings were performed at 450 nm.

20) Enzymatic treatments

MCF-7 membrane extracts were seeded into 96 wells plates (5 ug protein per well), dried overnight at 37° C., and were separately incubated for 1 hr. at 37° C. with the following enzymes (Sigma): trypsin (2.5 mg/ml), proteinase K (2 mg/ml) and neuraminidase (40 U/ml). After washing with PBS, wells were blocked with 100 ul of 1% BSA in PBS for 1 hr. The persistence of epitope reactivity was determined by ELISA as described above.

21) Other treatments a) Methanol: a sample of membrane extract seeded and dried as before, was treated with 100 ul of methanol during 30 min. at 0° C.; b) Heat: prior to seeding, the membrane extract was heated for 30 min. at 100° C. and centrifuged at 1,000×g for 5 min. In both cases washing, blocking and reactivity determination were performed as above.

22) Determination of monoclonal antibody FC-2.15 in patients' serum

Serum samples obtained from patients under treatment with monoclonal antibody FC-2.15 were evaluated for monoclonal antibody levels. 50 ul of a 1/50 dilution of goat serum anti-mouse IgM were seeded into 96 wells plates and dried overnight at 37° C. After blocking with 5% non-fatty milk for 2 hrs. at room temperature, 100 ul of serum samples (diluted 1:1 with PBS) were added and incubated overnight at 4° C. After several washings with 0.1% BSA in PBS, samples were incubated for 90 min. at room temperature with a 1/250 dilution of a peroxidase-conjugated rabbit antiserum anti-mouse immunoglobulin. After several washings, color was developed with 1 mg/ml o-phenylenediamine as described above. Readings were performed at 415 nm and compared with known amounts of MAb run in parallel.

23) Sequencing of the variable regions of heavy and light chains of monoclonal antibody FC-2.15

Total RNA was obtained from exponentially growing FC-2.15 hybridoma cells. For RNA preparation, cells were washed twice with PBS and resuspended in buffer containing sodium isothiocyanate. Total RNA was obtained by the acid phenol method as described (Chomczynski, P. and Sacchi, N., (1987), "Single step method of RNA isolation by acid guanidinium thiocyanate-phenol-chloroform extraction". *Anal. Biochemistry,* 162:156–159). First strand cDNA was synthesized from 1 ug of total RNA in 20 ul of a reaction mixture containing reverse transcriptase buffer, 250 uM of dNTPs mixture, 300 ng of specific oligonucleotide primer and 20 units of M-MoLV reverse transcriptase. Samples were incubated for 2hr at 42° C.

The specific oligoprimers used for the reverse transcription are complementary either to the constant region of the u chain (primer CHMu) mRNA, or to the constant region of the kappa chain (primer CK2) mRNA. The oligoprimer sequences are the following:

CHMu: CATTGGGAAGGACTGACTC SEQ. ID. NO.:1
CK2: TGGATACAGTTGGTGCAGC SEQ. ID. NO.:2

Two ul of the reverse transcription product were amplified by the Polymerase Chain Reaction (PCR). A standard PCR reaction was performed in 50 ul volume containing 125 uM dNTPs, 1.5 mM $MgCl_2$, 50 mM KCl, 2 units of Taq pol and 300 ng of oligoprimers CHMu or CK2 and VHB or VKB-2 as appropriate.

The amplification primers VHB and VKB-2 were designed to be complementary to the cDNA sequence of the conserved N-terminal region of the heavy and light chains. The oligoprimers sequence are as follows:

VHB: AGGTGCAGCTGCAGGAGTCTGG SEQ. ID. NO.:3

CAACA

VKB-2: GATATTGTGATGACCCAGTCTCCA SEQ. ID. NO.:4

Samples were amplified for 35 thermal cycles under the following conditions: 90 sec at 94° C., 90 sec at 52° C. and 2 min. at 72° C.

Amplified samples were resolved on 1.5% Sea Kem agarose. The desired products (350–370 bp length for the heavy chain and 330 bp length for the light chain) were electroeluted. After "polishing" and kination with Klenow and T4 polynucleotide kinase respectively. PCR products were subcloned in the Sma I site of bacterial alkaline phosphatase treated-pUC18 vector. Recombinant vector containing the desired insert was obtained through Miniprep Spun Columns, purified and sequenced using the CueCard T7 Sequencing Kit following manufacturer's instructions. 24) Localization of monoclonal antibody FC-5.01 in breast cancer tumors grown in nude mice by immunoscintigraphy A) Preparation of F(ab')$_2$ and radiolabelling.

F(ab')$_2$ fragments were generated from FC-5.01 purified MAb, or from a non-specific IgG 2a MAb UPC 10 (Sigma Chemical Co, St Louis). Briefly, 1.5 mg of IgG were digested with 45 ug pepsin in acetate buffer, during 4 hr at 37° C., as previously described (Lamoyi, E., (1986), "Preparation of F(ab')$_2$ Fragments from mouse IgG of various subclasses". *Meth. Enzymol.*, 121:652–663). Fragments were concentrated and purified by passing through Centricon CM 30 columns.

Fifty ug of purified MAb FC-5.01 and the F(ab')$_2$, as well as the whole UPC 10 IgG and its derived F(ab')$_2$ fragments were radiolabelled with $^{125}$I using the iodogen method (Fraker, P. J. and Speck, J. C., (1978), "Protein and cell membrane iodinations with a sparingly soluble chloroamide, 1,3,4,6-tetrachloro-3a,6a-diphenyl-glycoluril. *Biochem. Biophys. Res. Commun.*, 80:849–857). The iodinated IgG (1.5–6 ug/ml) was separated from free $^{25}$I by passing through Sephadex G-25 columns.

B) in vivo distribution and immunoscintigraphy.

For in vivo distribution studies, nude mice bearing contralateral human breast cancer IIB-BR-G tumors were injected i.p. with 10 ug of iodinated IgG or F(ab')$_2$. At different times, mice were sacrificed, the different organs weighed and the radioactivity counted. For immunoscintigraphy studies, mice bearing IIB-BR-G tumors in both flanks were given i.p. 300 uCi of $^{125}$I FC-5.01 or UPC 10. Serial scintiphots were obtained from each animal at different days postinjection, after analysis with a gamma camera equipped with a pinhole collimator (aperture, 0.25 inch).

RESULTS

Figure 2:
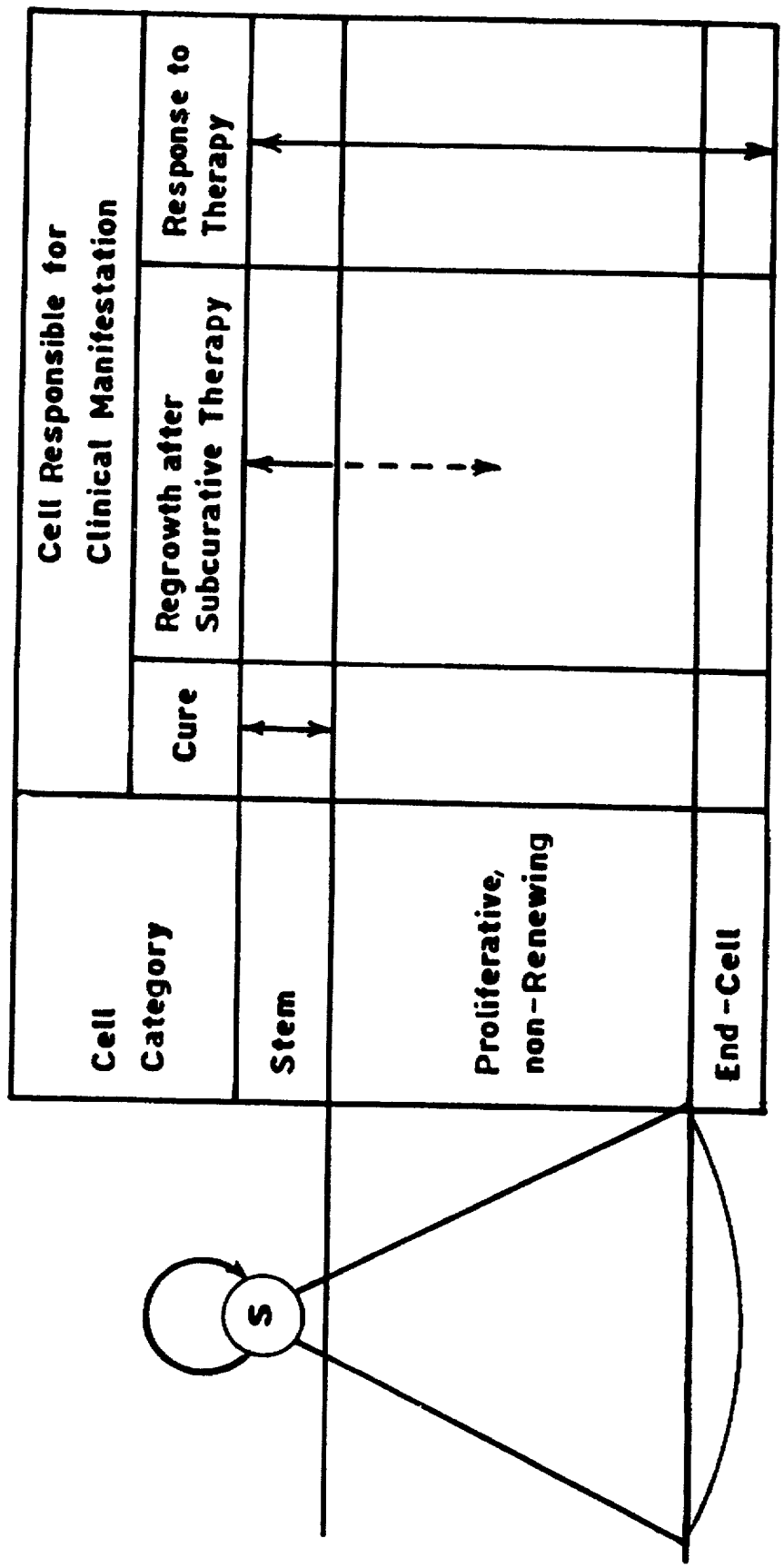
FIG. 2 is a schematic diagram of tumor evolution and clinical responses observed after the elimination of different subpopulations of the cellular hierarchy.
Figure 3:
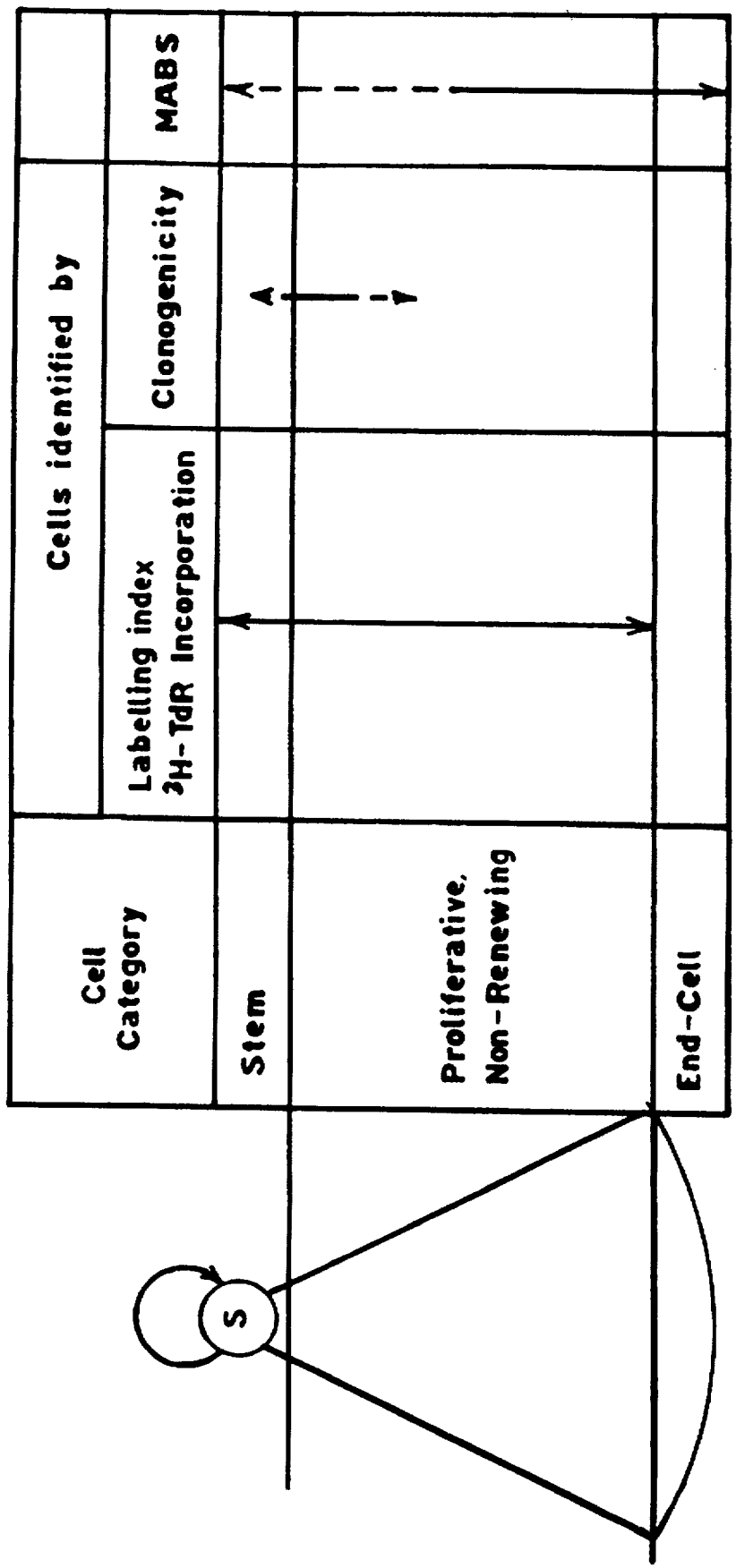
FIG. 3 is a schematic diagram showing possible methods for the identification of the different subpopulations of such hierarchy.
Figure 4A:
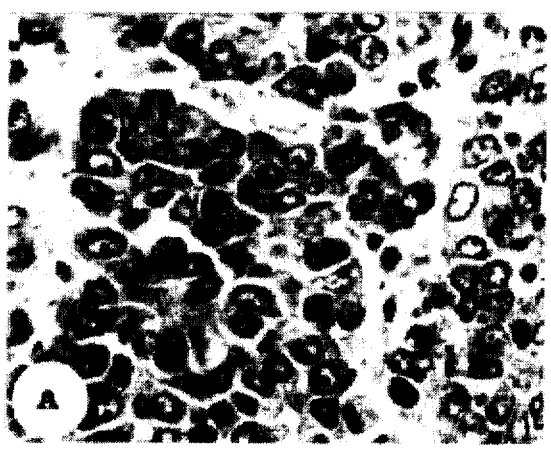
Figure 4B:
Figure 4C:
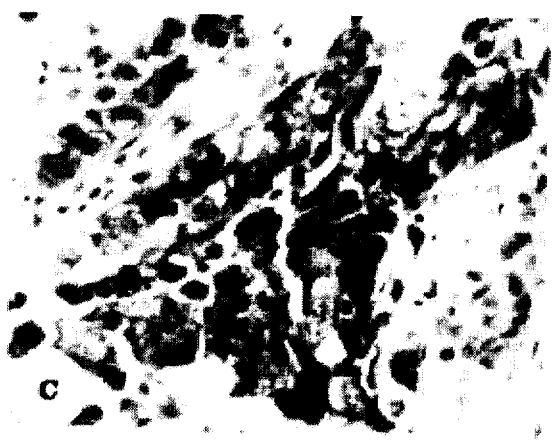
Figure 4D:

1. Reactivity of monoclonal antibodies FC-2.15 and FC-5.01 with human breast carcinomas Table 1 provides a summary of the reactivity data obtained using immunohistochemical techniques. Fifty nine tumors were analyzed, of which 34 (58%) were NOS, 11 (19%) were ductal carcinomas with tubular formation, 10 (17%) were lobular, 2 (3%) were medullar, 1 (1.7%) mucinous and 1 (1.7%) histiocytoid. Positive tumors were considered those with >10% of positive cells. As observed, both MAbs react with more than 90% of breast tumors of different histologies. The Table also reveals that FC-2.15 and FC-5.01 epitopes are expressed by the great majority of the tumor cells in positive tumors. In each case the reactivity was independent of the histologic tumor type (see Table 2 as an example for MAb FC-2.15). In each case, staining with MAbs was confined to epithelial and myoepithelial cells, and no reactivity was observed with stromal fibroblasts, lymphocytes or red blood cells. Histological sections showing the reactivity of MAb FC-2.15 with breast carcinomas are showan in FIGS. 4A and B. Staining is positive in the cytoplasm and membrane of tumor cells (FIG. 4A), and some tumors revealed a considerable reinforcement of the cell membrane (FIG. 4B). The distribution of positive cells for a specific antigen was frequently heterogeneous within a single tumor (FIG. 4B).

2. Comparison between monoclonal antibodies FC-2.15 and FC-5.01 with previously described monoclonal antibodies recognizing breast cancer associated antigens The antibodies described herein are capable of recognizing antigens expressed by proliferating cells. This property is essential to the therapeutic efficacy of any antibody. Monoclonal antibody FC-2.15 recognizes the majority of tumor cells engaged in DNA synthesis. This constituting an important improvement, since most of the previously reported monoclonal antibodies that recognize human breast cancer associated antigens do not share this property; they recognize the differentiated cell progeny of human breast cancer tumors.

First, experiments were performed to determine the percentage of proliferating cells detected by MAbs FC-2.15 and FC-5.01. To this end, tumor samples obtained from 16 patients affected with breast cancer were incubated with ($^3$H) thymidine, and the number of cells engaged in DNA synthesis and their antigenic reactivity with the MAbs were simultaneously determined. A detailed study performed with MAb FC-2.15 shows that, on average, almost 90% of proliferating cells express the specific epitope (see table 3). Similar studies performed with MAb FC-5.01 in 5 samples, show that MAb FC-5.01 reacted on average with 70% of proliferating cells.

Second, reactivity with tumor proliferating cells of MAb FC-2.15 was compared with that of monoclonal antibodies previously described that reacted with breast cancer associated antigens. Tumor cells from 28 primary breast carcinomas were analyzed for their expression of different tumor associated antigens and DNA synthesis as previously described. The monoclonal antibodies utilized and the antigens (Ags) they recognize were the following: FC-2.15 (Ag 2.15); B1.1 (Ag CEA B1.1) (see above Colcher, D. et al, 1981, ibid); COL-12 (Ag CEA $_{COL-12}$) (Muraro, R., Wunderlich, D., Thor, A., Lundy, J., Noguchi, P., Cunningham, R., Schlom, J. (1985): "Definition by monoclonal antibodies of a repertoire of epitopes on carcinoembryonic antigen differentially expressed in human colon carcinomas versus normal adult tissues". *Cancer Res.*, 45:5769–5780); 436 (Ag polymorphic epithelial mucin, PEM) (Nuti, M., Turchi, V., Masci, A. M., Viacava, P., Rughetti, A., Castagna, M., Frati, L. (1992): "Characterization of monoclonal antibody 436 recognizing the ARG-PRO-ALA-PRO sequence of the polymorphic epithelial mucin (PEM) protein core in breast carcinoma cells". *Int. J. Biol. Markers*, 7:71–79); B72.3 (Ag TAG-72) (Nuti, M., Teramoto, Y., Mariani-Costantini, R., Horan Hand, P., Colcher, D., Schlom, J., (1982), "A monoclonal antibody (B72.3) defines patterns of distribution of a novel tumor associated antigen in human mammary carcinoma cell populations". *Int. J. Cancer*, 29:539–545); MBr1 (Ag CaMBr1) (see above Menard, S. et al., (1983), ibid), B6.2 (Ag non-cross reacting antigen, NCA) (Colcher, D. et al., (1983), ibid); 57 (Ag P170) (Cenciarelli, C., Currier, S. J., Willingham, M. C. et al., (1991), "Characterization by somatic cell genetics of a monoclonal antibody to the MDR1 gene product (P-glycoprotein): determination of P-glycoprotein expression in multi-drug-resistant KB and CEM cell variants". *Int. J. Cancer*, 47:533–543); ER-ICA (commercial kit from Abbott Laboratories) (Ag ER); PgR-ICA (commercial kit from Abbott Laboratories) (Ag PgR).

Results are shown in Table 4 (extracted from Ballare, C., Bravo, A. I., Turchi, V., Nuti, M., Yomha, R., Schiaffi, J., and Mordoh, J., (1993), "Marker expression in human breast cancer" *Annals of the N.Y. Academy of Sciences*, 698:143–147) where it may be observed that, with the exception of the monoclonal antibody reacting with PgR and ER, the other MAbs recognize at least 57% of primary breast carcinomas. However, only the monoclonals recognizing FC-2.15 antigen and PEM antigen are expressed in average by nearly 80% of tumor cells. Most important, when the thymidine labelling index of the different antigen-expressing cell populations was analyzed, it was observed that the TLI of the 2.15-positive cell population was significantly higher than those of the other antigen-positive populations (Table 4). FIG. 5 exemplifies the above presented data by showing that proliferating cells are not recognized by the anti-CEA monoclonal antibody named COL-12 (FIG. 5A). On the other hand, every proliferating cell is recognized by monoclonal FC-2.15 (FIG. 5B).

These data provide evidence that MAb FC-2.15 recognizes different cellular subpopulations than the monoclonal antibodies previously described. These results are also evidence that MAbFC-2.15 recognizes a previously undescribed antigen. Further evidence is provided below that the recognized antigen is new and different from those previously known.

3. Reactivity of monoclonal antibodies FC-2.15 and FC-5.01 with human benign mammary pathologies When the reactivity of these antibodies with human benign mammary pathologies was tested, a positive reaction was observed with mammary adenosis, fibroadenomas, typical hyperplasias and fibrosis (Table 5). The number of positive cells was in general scarce and the staining intensity (on a scale of 1+ to 5+) was only 1+ (FIG. 6A). Nevertheless, when the tubules of hyperplastic lesions were composed of three or more cell layers, intracytoplasmic staining similar to that found in tumor tissue was observed (FIG. 6B). Intraluminal secretion was likewise observed in several cases of adenosis with epithelial hyperplasia (not shown).

4. Reactivity of monoclonal antibodies FC-2.15 and FC-5.01 with human neoplasias other than breast cancer Table 6 summarizes the general reactivity of monoclonal FC-2.15 with non-mammary neoplasias. The table reveals that reactivity was not restricted to mammary neoplasias (see also FIGS. 4C and 4D). MAb FC-2.15 reacted intensely with colon and thyroid carcinoma and to a lesser degree with other carcinomas (table 6). The reactivity of FC-2.15 with melanomas tended to be light, whereas FC-5.01 was much more positive (not shown). FC-2.15 was negative with liposarcoma and leiomyosarcomas.

In addition to breast carcinomas and melanomas, FC-5.01 strongly reacted with colon carcinomas. In addition, FC-5.01 has shown a positive reactivity with leiomyosarcomas (not shown).

5. Reactivity of monoclonal antibodies FC-2.15 and FC-5.01 with normal human tissues Table 7 shows the pattern of reactivity of monoclonal FC-2.15 with normal tissues. MAb FC-2.15 did not react with the following normal tissues: breast (FIG. 6C), liver, lung, thyroid and lymphocytes. Whereas most of the tissues show scarce to moderate reactivity, strong reactivity was observed with myeloid bone marrow, peripheral granulocytes, kidney (proximal convolute tubules), spleen (red pulp) and large bowel. On the other hand, FC-5.01 reacted with normal thyroid cells and some Kupffer cells in liver. In addition, FC-5.01 reacted with pancreatic acini, proximal convoluted tubules of the kidney, and parafollicular cells of the thyroid. FC-5.01 was completely negative with peripheral granulocytes and lung tissue.

6. Reactivity of monoclonal antibodies with cell lines in tissue culture

Monoclonal antibody FC-2.15 was positive with exponentially growing human breast cancer MCF-7 cells and T47-D cells but did not react with human breast cancer IIB-BR-G cells and MDA-MB-231 cells, nor with human melanoma IIB-MEL-J cells. MAb FC-5.01 reacted with all of these human cell lines (the percentage of reacting cells was, on average, higher than 50%).

7. Antibody-mediated complement cytotoxicity of MAb FC-2.15 on cells isolated from human breast carcinomas, breast cancer cell lines and normal bone marrow Monoclonal antibodies may possess a direct cytotoxic effect on tumor cells, requiring only serum C' to act, or they can mediate cellular cytotoxicity, requiring the addition of lymphocytes or macrophages (i.e., ADCC or antibody-dependent-cell-cytotoxicity). In these experiments, we have addressed the direct cytotoxic effect. We have tested the capacity of our monoclonal antibodies to eliminate cancer cells from human primary tumors after cellular dissociation and purification using the soft-agar clonogenic capacity method (see above Buick, R. N. and Fry, S. E., (1980), ibid). Table 8 shows the effect of antibody-mediated—C'-cytotoxicity on the colony formation capacity of tumor cells isolated from three primary breast carcinomas and one axillary lymph node metastasis. Similar experiments were performed with exponentially growing MCF-7 cells. The results shown in Table 8 demonstrate that MAb FC-2.15 notably reduced the clonogenic capacity of breast tumor cells. Finally, the action of MAb FC-2.15 on normal bone marrow clonogenic cells was assayed, due to its reactivity with the myeloid progeny of normal bone marrow cells. Table 8 shows that FC-2.15 did not affect the clonogenic capacity of bone marrow stem cells.

Monoclonal antibody FC-5.01 was not tested on bone marrow cells due to the lack of reactivity with these cells. Although FC-5.01 reacted with every human melanoma and breast cancer cell line tested, no clear effect on the clonogenic capacity of the different human cell lines was observed (percentage of inhibition around 10%).

8. Antigen characterization

A) Monoclonal FC-2.15.

By Western blots, three major bands of 160 kDa, 130 kDa and 115 kDa were detected in membrane extracts of MCF-7 tumors grown in nude mice as well as in samples obtained from human breast carcinomas (FIG. 7). We investigated whether FC-2.15 recognized similar Ags in normal tissues. Membrane extracts from normal peripheral granulocytes were analyzed. Three major bands of 250 kDa, 185 kDa and 105 kDa were detected. Since granulocytes are known to express Non Cross-reacting Antigen (NCA), which has some cross-reactivity with CEA, membrane extracts were assayed with B1.1 and B6.2, MAbs directed against CEA and NCA respectively. B1.1 detects two bands of 180 kDa and 90 kDa, whereas only a 90 kDa band is detected with B6.2 (FIG. 7). No reactivity with FC-2.15 could be demonstrated in cytoplasmic extracts of tumor cells or granulocytes (data not shown).

In order to determine if the reactive epitope of Ag 2.15 contains a carbohydrate, a periodate oxidation that destroys adjacent sugar hydroxyl residues was performed on MCF-7 cells grown in culture. The reactivity of the tumor cells with MAb FC-2.15 was partially inhibited by 10 mM periodate (47.1±7% inhibition; mean±standard deviation of three different experiments performed in duplicate). Under the same conditions MAb MBrl reactivity towards the carbohydrate epitope CaMBrl (see above Menard S. et al, 1983,ibid) was similarly inhibited (56.3±17% inhibition). These results suggest that the reactive epitope of Ag 2.15 includes a carbohydrate moiety. Other treatments have shown that the epitope reactivity was diminished by trypsin and proteinase K but was not affected by methanol, heating or neuraminidase (data not shown).

These characteristics of the Ag 2.15 allow it to be differentiated from previously described breast cancer associated antigens: 1) CaMBrl, a glycolipid and 145 kD and 270 kD glycoprotein associated carbohydrates recognized by MAb MBr 1 (see above Menard et al, ibid); 323 A/3, a 43 kD glycoprotein present in 36% of breast carcinomas and absent in normal tissues with the exception of kidney and colon (Tandon, A. K., Clark. G. M., Chamness, G. C. and McGuire, W. L., (1990), "Association of the 323/A3 surface glycoprotein with tumor characteristics and behavior in human breast cancer". Cancer Res, 50:3317–21); 3) 436 Ag (200 kD Mr) which belongs to the polymorphic epithelial mucin family and which is absent in normal bone marrow (see above Nuti et al, 1992, ibid); and TAG-72, a high Mr antigen (Mr 1×10$^6$ kD) with mucin-like properties (see above Nuti et al, 1982, ibid).

B) Monoclonal FC-5.01.

FIG. 8 shows a western blot performed using a human metastatic melanoma membrane extract. Similar results were obtained when MCF-7 and IIB-BR-G membrane extracts were used. MAb FC-5.01 reacted with a high Mr protein with low mobility in a 7.5% SDS-polyacrylamide gel. This reactivity was lost when the gel was run under reducing conditions. Heating and trypsin or proteinase K digestion greatly reduced the antigen reactivity, while methanol addition had no effect. The epitope does not contain a carbohydrate residue, since no deleterious effect on antigen reactivity was seen after treatment with sodium periodate. These results demonstrate that FC-5.01 antigen is different from FC-2.15 antigen and that the MAbs recognize different epitopes.

9. Effect of monoclonal FC-2.15 on granulocytes and tumor cell agglutination

On the basis of the following experimental evidence:
a) the reactivity of monoclonal FC-2.15 with the myeloid progeny of bone marrow,
b) the decrease in total number of circulating granulocytes in patients' blood samples, following monoclonal FC-2.15 infusion (see below), and
c) the reactivity of monoclonal FC-2.15 with membrane antigens, both in granulocytes and tumor cells, the interaction of monoclonal FC-2.15 with granulocytes and tumor cells was further studied in vitro.

Figure 9A:
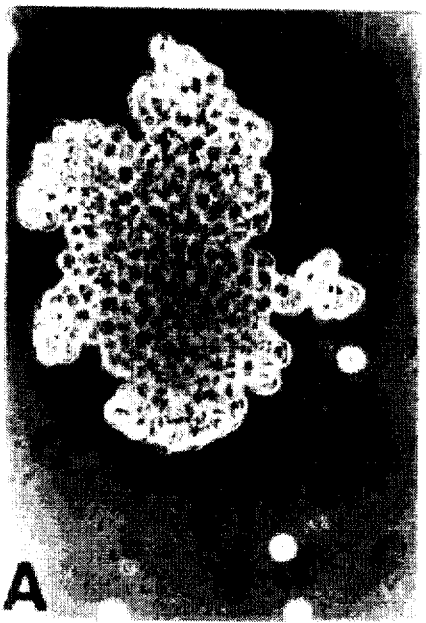
Figure 9B:
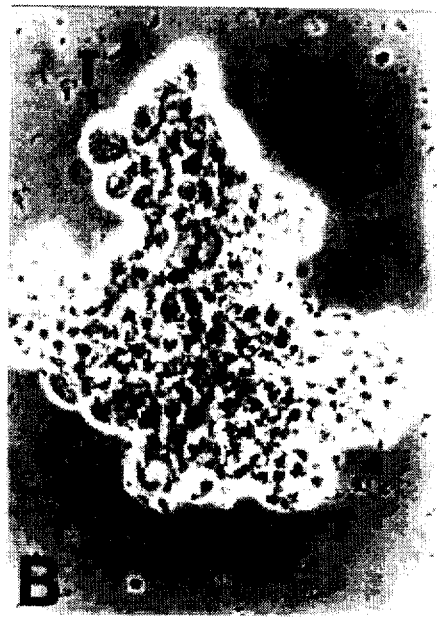
Figure 9C:
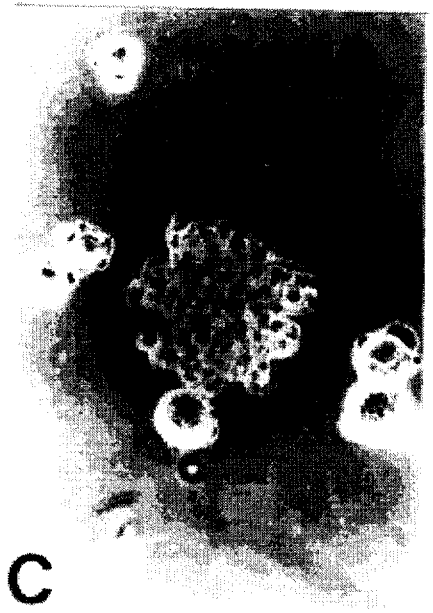
Figure 9D:
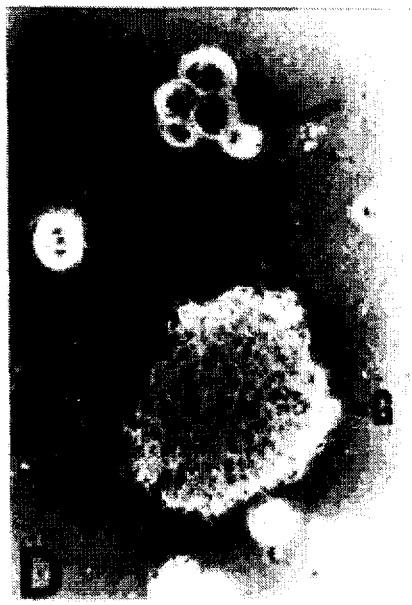

FIG. 9A shows that peripheral granulocytes incubated with monoclonal FC-2.15 formed large aggregates. Mixed aggregates between granulocytes and tumor cells (expressing FC-2.15 antigen) were observed after incubation with monoclonal FC-2.15 (FIG. 9B). On the other hand those mixed clumps were not observed when FC-2.15 antigen non-expressing cells were incubated with granulocytes under the same conditions (FIGS. 9C and 9D). In addition, a monoclonal IgM (monoclonal 436) recognizing a mucin protein expressed by breast cancer cells (see above Nuti, M. et al, (1992), ibid) but not by granulocytes, was not able to induce this mixed aggregation, suggesting the specificity of this effect.

IN VIVO STUDIES

Studies in murine models with MAb FC-5.01.

In order to study the use of MAb FC-5.01 for in vivo tumor detection, nude mice bearing contralateral IIB-BR-G tumors were i.p. injected with iodinated IgG or F(ab')$_2$ derived fragments as described above. MAb FC-5.01 distribution in tumor-bearing mice showed a specific tumor localization several days after injection (FIG. 10). A more prominent accumulation in tumor tissues was seen after 7–8 days (see FIG. 10 and table 9). This retention of MAb FC-5.01 in tumor tissue was specific (see, for comparison, the biodistribution of control IgG in FIG. 10 and table 9). A tumor: normal tissue ratio of 4 or more was reached by comparing FC-5.01 accumulation in tumor with that observed in liver and kidney (per gr of tissue). Further experiments were performed by studying the biodistribution of F(ab')$_2$ fragments. Tumor:normal tissue ratio for MAb FC-5.01 F(ab')$_2$ reached a peak 48 hr after injection in tumor-bearing mice (table 10). No tumor specific retention of UPC 10 F(ab')$_2$, fragments was observed, and most of the radioactivity remained in blood, kidney and skin (table 10). However, when the results were expressed as the percentage of radioactivity per gr of tissue, it was observed that F(ab')$_2$ fragment retention in tumors was markedly reduced compared with whole FC-5.01 IgG (for comparison see table 9 and 11, in bold).

Phase I Clinical Trial

A Phase I clinical trial (Res. 449/90) was recently authorized by the Ministry of Health and Social Welfare of Argentina to study the toxicity and optimum dosage of different monoclonal antibodies in patients with advanced cancer. 11 patients were enrolled in this study. A minimal toxicity was observed and no death was associated with the monoclonals therapy.

The therapeutic efficacy of monoclonal FC-2.15 was demonstrated in a patient with advanced breast carcinoma. The patient (ASR), 43 years-old woman, with metastatic breast cancer lesions in liver, lung and bone (see FIG. 11, upper panel, December 1992 for basal status of liver metastases) which were resistant to hormone therapy and chemotherapy, received a total dose of 98 mg of monoclonal antibody FC-2.15. The antibody packaged in vials was diluted immediately before infusion in 200 ml saline containing 5% human albumin. The antibody was given in four i.v. infusions according to FIG. 12, starting on Jan. 4, 1993. During treatment, no significant toxic effects were observed, only a mild hyperthermia (below 37.8° C.) which rapidly resolved with paracetamol. 29 days after starting the treatment, a decrease in the size and number of hepatic lesions was observed (FIG. 11, middle pannel, Feb. 2, 1993). This regression became more pronounced 106 days after the treatment was started (lower pannel, Apr. 20, 1993) and this remission was still observed 6 months post-therapy. The patient experienced neither allergic effects nor renal or hepatic toxicity as determined by blood samples analysis performed on days 7, 14, 30 and 60 post-therapy. Therefore, it can be concluded that treatment with monoclonal FC-2.15 can induce the regression of visceral metastases in patients with advanced breast carcinomas.

Pharmacokinetics

FIG. 12 (upper pannel) shows the serum concentrations of monoclonal FC-2.15 in patient ASR. Levels of 4 ug/ml of circulating FC-2.15 were obtained during the first infusion. This level decreased to 2 ug/ml after the second infusion and was even lower after the third infusion of monoclonal FC-2.15, most probably due to the development of a human antimurine antibody (HAMA) response. We also observed an immediate and profound decrease in the level of circulating granulocytes, which recovered at the end of the infusion. Interestingly, this recovery was accompanied by the appearance, in circulation, of immature forms. Total lymphocyte number was less affected by FC-2.15 monoclonal administration.

FIG. 12 also shows the pharmacokinetics of monoclonal FC-2.15 in a patient (HDF) carrying a thyroid medullar carcinoma. This patient was given 210 mg of FC-2.15 (3.85 mg/Kg weight) in i.v. infusions as described in FIG. 12. According to the pharmacokinetics parameters obtained after the first infusion, a serum $t_{1/2}$ of approximately 9 hr was calculated for monoclonal FC-2.15. An immediate decrease in circulating granulocytes was observed during the first hour of infusion, which rapidly recovered at the end of the infusion. Interestingly, these effects were observed with the three infusions. Most important, no evidence of HAMA response was observed in this patient since comparable levels of circulating FC-2.15 were measured throughout the course of FC-2.15 treatment.

Sequencing Of The V Region Of Monoclonal Antibody FC-2.15

FIG. 13 shows the nucleotide and amino acid sequence of the V regions of the FC-2.15 heavy and light chains. Both sequences were entered in a protein sequence data bank (Laser Gene Program, DNA star) and the following results obtained: The variable region of the light chain shows a high degree of homology with Abs which bind phosphatidyl choline (Pennell, C. A., Maynard, E., Arnold, L. W., Haughton, G. and Clarke, S. H., (1990), "High frequency expression S107 VH genes by peritoneal B cells of B10.H-2aH 4bP/WTS mice. 145:1592-1597). The variable region of the heavy chain was found to have a high degree of homology with MAbs reacting with polysaccharide antigens (Bonilla, F. A., Zagbouani, H., Rubin, M. and Bona, C., (1990), "V kappa gene usage, idiotype expression, and antigen binding among clones expressing the VHX24 gene family derived from naive and anti-idiotype immune immune Balb/c mice". J Immunol., 145:616–622).

REFERENCES

References are provided as they appeared in the text. (not by alphabetical order).

Buick, R. R. and Pollack, M. N., (1984), "Perspectives on clonogenic tumor cells, stem cells and oncogenes", Cancer Res., 44:4909–4918.

Bravo, A. I., Sorin, I., Guman, N. and Mordoh, J., (1985) "Carcinoembryonic antigen and differentiation in human breast cancer", J. Exp. Clin. Res., 4:3–10.

Sorin, I., Bravo, A. I., Podhajcer, O. L., Bover, L., Loza, J. Sousa Martinez, F., Guman, N. and Mordoh, J., (1988), "Analysis of DNA synthesis and carcinoembryonic antigen expression in human breast cancer", J. Exp. Clin. Cancer Res., 7:35–42).

Jensen, E. V., (1975), "Estrogen receptors in hormone-dependent breast cancers", Cancer Res., 35:3362–3364.

Podhjcer, O. L., Bravo, A. I., Sorin, I., Guman, N., Cerdeiro, R. and Mordoh, J., (1986), "Determination of DNA synthesis, estrogen receptors, and carcinoembryonic antigen in isolated cellular subpopulations of human breast cancer". Cancer, 58:720–729.

Ballare C., Bravo A. I., Laucella S., Sorin I., Cerdeiro R., Loza J., Sousa Martinez F., Guman N. and Mordoh J. (1989): "DNA synthesis in estrogen receptor - positive human breast cancer takes place preferentially in estrogen receptor-negative cells". Cancer 64: 842–848.

Resnicoff M., Medrano E. E., Podhajcer O. L., Bravo A. I., Bover L. and Mordoh J. (1987): "Subpopulations of MCF-7 cells separated by Percoll gradient centrifugation: A model to analyze the heterogeneity of human breast cancer". Proc. Natl. Acad. Sci. 84 : 7295–7299.

Bover L., Barrio M., Slavutsky I., Bravo A. I., Quintans C., Bagnati A., Lema B., Schiaffi J., Yomha R. and Mordoh J. (1991): "Description of a new human breast cancer cell line IIB-Br-G, established from a primary undifferentiated tumor". Breast Cancer Research and Treatment 19:47–56.

Galfre G. and Milstein C. (1981): "Preparation of monoclonal antibodies: strategies and procedures". Meth. Enzymol. vol 73,part B, 3–46.

Kearny J. F., Radbruch A., Liesegang B., and Rajewsky K. (1979). "A new mouse myeloma cell line that has lost immunoglobulin expression but permits the construction of antibody-secreting hybrid cell lines) J. Immunol. 132: 1548–1550.

Soule H. D., Vazquez J., Long A., Albert S. and Brennan M. A. (1973): "A human cell line from a pleural effusion derived from a breast carcinoma". J. Natl. Cancer Inst. 51: 1409–1415.

Keydar I., Chen L., Karby S., Weiss F. R., Delarea J., Radu M., Chaitcick S., Brenner H. J. (1979): "Establishment and characterization of a cell line of human breast carcinoma origin". Eur. J. Cancer 15: 659–670.

Cailleau R., Young R., Olive M. and Reeves W. J. (1974): "Breast tumor cell lines from pleural effusions". J. Natl. Cancer Inst. 53: 661–674.

Guerra L., Mordoh J., Slavutsky I., Larripa I. and Medrano E. E.(1989): "Characterization of IIB-MEL-J: A new and highly heterogeneous human melanoma cell line". Pigment Cell Res. 2: 504–509.

Podhajcer O. L., Resnicoff M., Bover L., Medrano E. E., Slavutsky I., Larripa I. and Mordoh J. (1988): "Effect of estradiol and tamoxifen on the anchorage-independent growth of the subpopulations derived from MCF-7 breast carcinoma cells: cytogenetic analysis of the stem cell subpopulation". Exp. Cell res. 179: 58–64.

Buick R. N. and Fry S. E. (1980): "A comparison of human tumor-cell clonogenicity in methylcellulose and agar culture". Br. J. Cancer 42: 933–936.

Hamburger A. W. and Salmon S. E. (1977): "Primary Bioassay of human tumor stem cells", Science 197: 461–463.

Ash R., Detrick R. and Zanjani E. D. (1981): "Studies of human pluripotential hemopoietic stem cell (CFU-GEMM) in vitro". Blood 58, 309–316.

Laemmli U. K. (1970): "Cleavage of structural proteins during the assembly of the head of bacteriophage T4". Nature Lond. 227:680–685.

Lowry O. H., Rosebrough N. J., Farr A. L. and Randall E. (1951): "Protein measurement with the Folin phenol reagent". J. Biol. Chem. 193:265–275.

Colcher D., Horan Hand P., Nuti M. and Schlom J.(1981): "A spectrum of monoclonal antibodies reactive with human mammary tumor cells". Proc Natl Acad Sci (USA) 78: 3199–203.

Colcher D., Horan Hand P., Nuti M. and Schlom J. (1983): "Differential binding to human mammary and non mammary tumors of monoclonal antibodies reactive with carcinoembryonic antigen". Cancer Invest. 1: 127–38.

Magnani J. L., Spitalnik S. L., and Ginsburg D. (1987): "Antibodies against cell surface carbohydrates: determination of antigen structure". Meth. Enzymol 138:195–202.

Menard S., Tagliabue E., Canevari S., Fossati G., Colnaghi M. I. (1983): "Generation of monoclonal antibodies reacting with normal and cancer cells of human breast". Cancer Res. 43: 1295–300.

Chomczynski P. and Sacchi N. (1987): "Single step method of RNA isolation by acid guanidinium thiocyanate-phenol-chloroform extraction". Anal. Biochemistry 162:156–159.

Lamoyi E. (1986): "Preparation of F (ab')$_2$ Fragments from mouse IgG of various subclasses". Meth. Enzymol. 121: 652–663.

Fraker P. J. and Speck. J. C. (1978): "Protein and cell membrane iodinations with a sparingly soluble chloroamide,1,3,4,6-tetrachloro-3a, 6a-diphenylglycoluril". Biochem. Biophys. Res. Commun. 80: 849–857.

Muraro R., Wunderlich D., Thor A., Lundy J., Noguchi P., Cunningham R., Schlom J. (1985): "Definition by monoclonal antibodies of a repertoire of epitopes on carcinoembryonic antigen differentially expressed in human colon carcinomas versus normal adult tissues". Cancer Res. 45: 5769–5780.

Nuti M., Turchi V., Masci A. M., Viacava P., Rughetti A., Castagna M., Frati L. (1992): "Characterization of monoclonal antibody 436 recognizing the ARG-PRO-ALA-PRO sequence of the polymorphic epithelial mucin (PEM) protein core in breast carcinoma cells". Int. J. Biol. Markers, 7: 71–79).

Nuti M., Teramoto Y., Mariani-Costantini R., Horan Hand P., Colcher D., Schlom J. (1982): "A monoclonal antibody (B72.3) defines patterns of distribution of a novel tumor associated antigen in human mammary carcinoma cell populations". Int. J. Cancer 29: 539–545.

Cenciarelli C., Currier S. J., Willingham M. C. et al. (1991): "Characterization by somatic cell genetics of a monoclonal antibody to the MDR1 gene product (P-glycoprotein): determination of P-glycoprotein expression in multi-drug-resistant KB and CEM cell variants". Int. J. Cancer 47: 533–543.

Ballare C., Bravo A. I., Turchi V., Nutti M., Yomha R., Schiaffi J. and Mordoh J (1994): "Marker expression in human breast cancer" Annals of the N.Y. Academy of Sciences 698: 143–147.

Tandon A. K., Clark G. M., Chamness G. C. and McGuire W. L. (1990): "Association of the 323/A3 surface glycoprotein with tumor characteristics and behavior in human breast cancer".Cancer Res 50,3317–21.

Pennell. C. A., Maynard E., Arnold L. W., Haughton G. and Clarke S. H. (1990): "High frequency expression S107 VH genes by peritoneal B cells of B10.H-2aH 4bP/WTS mice". J Immunol 145, 1592–1597.

Bonilla F. A., Zaghouani H., Rubin M. and Bona C. (1990): "V kappa gene usage, idiotype expression, and antigen binding among clones expressing the VHX24 gene family derived from naive and anti-idiotype immune immune Balb/c mice". J Immunol. 145, 616–622.

TABLE 1

GENERAL REACTIVITY OF MONOCLONAL ANTIBODIES WITH HUMAN BREAST CARCINOMAS

| MAb | positive tumors (a) | positive cells (b) |
|---|---|---|
| FC-2.15 | 31/33 (94) | 79.6 ± 13.7 |
| FC-5.01 | 35/36 (97) | ++++(90%) |

(a) Positive cases / total cases (percentage)

(b) Percentage of positive cells expressed as mean ± SD or as: + = 0–25%; ++ = 26–50%; +++ = 51–75%; ++++ = 76–100%.

TABLE 2

REACTIVITY OF FC-2.15 WITH HUMAN PRIMARY BREAST CANCER

| Histological type | Positivity | | |
|---|---|---|---|
| | Tumors* | Cells+ | Intens.++ |
| ID with tubules | 4/4 | 2.2+ | 1.5+ |
| ID, NOS | 16/17 | 2.7+ | 2.0+ |
| ID, medullary | 2/2 | 2.5+ | 2.5+ |
| Infiltrating lobular | 8/8 | 2.6+ | 2.1+ |
| Colloid carcinoma | 1/1 | 2.0+ | 1.0+ |
| Histiocytoid | 0/1 | — | — |
| Positive/Total | 31/33 | | |

*number of positive tumors/ total tumors;
+Average percentage of positive tumor cells: 1+ = 0–33%; 2+ = 34–66%; 3+ = 67–100%. Total tumor cells were taken as 100%;
++Intensity of the reaction: 1+ = weakly positive; 2+ = moderately positive; 3+ = strongly positive.
ID = intraductal;
NOS = not otherwise specified.

TABLE 3

REACTIVITY OF FC-2.15 WITH PROLIFERATING BREAST CANCER CELLS

| Sample | FC-2.15/total cells (%) (a) | FC-2.15/prolif. cells (%) (b) |
|---|---|---|
| 1 | 68 | 79 |
| 2 | 95 | 92 |
| 3 | 96 | 100 |
| 4 | 100 | 100 |
| 5 | 93 | 100 |
| 6 | 96 | 92 |
| 7 | 62 | 86 |
| 8 | 59 | 66 |
| 9 | 65 | 95 |
| 10 | 75 | 87 |
| 11 | 71 | 81 |
| 12 | 79 | 86 |
| 13 | 78 | 86 |
| 14 | 65 | 75 |
| 15 | 87 | 100 |
| 16 | 85 | 94 |
| Mean ± SD | 79.6 ± 13.7 | 88.7 ± 9.9 |

(a): Percentage of total tumor cells reacting with MAb FC-2.15;
(b): Percentage of proliferating cells reacting with MAb FC-2.15.

TABLE 4

MARKER EXPRESSION IN PRIMARY BREAST TUMORS

| Marker | Positive tumors (%) (a) | Positive cells (%) (b) | Marker-positive DNA-synthesizing Cells (%) (c) |
|---|---|---|---|
| 2.15 | 93 | 85.7 + 10.7 | 91.3 + 13.7 |
| PEM | 100 | 79.1 + 13.2 | 64.7 + 21.0 |
| P170 | 71 | 53.2 + 25.7 | 43.9 + 27.4 |
| NCA | 86 | 56.0 + 25.9 | 41.7 + 18.5 |
| CBA(B1.1) | 89 | 58.3 + 20.5 | 29.6 + 19.0 |
| ER | 50 | 41.4 + 19.3 | 27.1 + 16.1 |
| PgR | 43 | 41.6 + 18.8 | 14.8 + 10.7 |
| CaMBr1 | 75 | 40.8 + 20.6 | 14.5 + 13.1 |
| TAG-72 | 82 | 41.7 + 20.1 | 13.2 + 12.0 |
| CEA(COL-12) | 57 | 34.8 + 22.3 | 3.2 + 5.8 |

(a) positive tumors were those with - 10% positive cells
(b) Mean ± SD. Average positive cells for each monoclonal antibody was calculated taking into account only positive tumors
(c) Mean ± SD. The total number of DNA-synthesizing cells was taken as 100%

TABLE 5

REACTIVITY OF MONOCLONAL ANTIBODIES WITH HUMAN BENIGN BREAST PATHOLOGIES

| Monoclonal antibody | Positivity (a) | Observations |
|---|---|---|
| FC-2.15 | 6/11 | Positivity in ducts. |
| FC-5.01 | 3/11 | Positivity in ducts. |

(a) Positive cases / total cases.

TABLE 6

REACTIVITY OF FC-2.15 WITH NEOPLASIAS

| | Positivity | | |
|---|---|---|---|
| Neoplasia | Tumors (a) | Cells (b) | Intensity (c) |
| Carcinomas | | | |
| Colon | 2/2 | 3+ | 3+ |
| Squamous (Skin) | 1/1 | 3+ | 1+ |
| Larynx | 1/1 | 1+ | 1+ |
| Uterus | 1/1 | 3+ | 1+ |
| Thyroid | 1/1 | 3+ | 3+ |
| Ovarian | 1/1 | 1+ | 2+ |
| Prostate | 1/1 | 3+ | 1+ |
| Kidney clear cell | 1/1 | 2+ | 1+ |
| Others | | | |
| Metastatic melanoma | 4/12 | 3+ | 1+ |
| Basocellular epithelioma | 1/1 | 1+ | 1+ |
| Hodgkin lymphoma (Sternberg cells) | 1/1 | 3+ | 3+ |
| Fibrohistiocytoma | 1/1 | 1+ | 1+ |
| Leiomyosarcoma | 0/1 | N | N |
| Liposarcoma | 0/1 | N | N |

(a) positive tumors/total tumors;
(b) cellular positivity
(c) staining intensity was measured as in Table 1.
N: negative

TABLE 7

REACTIVITY OF FC-2.15 WITH NORMAL TISSUES

| | Positivity | | |
|---|---|---|---|
| Tissue | samples (a) | cells (b) | intensity (c) |
| Kidney (Proximal convolute tubules) | 1/1 | 3+ | 3+ |
| Myeloid bone marrow | 8/8 | 3+ | 3+ |
| Peripheral granulocytes | 7/7 | 3+ | 3+ |
| Spleen | 1/1 | | |
| White pulp | | — | — |
| Red pulp | | 3+ | 3+ |
| Large bowel | 1/1 | 3+ | 3+ |
| Stomach | 1/1 | 2+ | 1+ |
| Endocervix | 1/1 | 2+ | 1+ |
| Endometrium | 1/1 | 2+ | 1+ |
| Adrenal gland | 1/1 | 1+ | 1+ |
| Skeletal muscle | 1/1 | 1+ | 1+ |
| Testis | 1/1 | 1+ | 1+ |
| Ovary | 1/1 | 1+ | 1+ |
| Small bowel | 1/1 | 1+ | 2+ |
| Epidermis | 1/1 | 1+ | 1+ |
| Sebaceous glands | 1/1 | 1+ | 1+ |
| Pancreatic acini | 1/1 | 1+ | 1+ |
| Brain | 1/1 | | |
| Neurons | | — | — |
| Axons | | 1+ | 1+ |
| Cerebellum | 1/1 | | |
| Neurons | | — | — |
| Axons | | 1+ | 1+ |
| Liver | 0/1 | — | — |
| Lung | 0/1 | — | — |
| Breast | 0/2 | — | — |
| Thyroid | 0/1 | — | — |
| Lymph nodes | 0/1 | — | — |

(a) Positive cases/Total cases;
(b) Positive cells were estimated as in Table 1;
(c) The intensity of the reaction was estimated as in Table 1.

TABLE 8

EFFECT OF FC-2.15 ON THE CLONOGENIC ABILITY OF BREAST TUMOR CELLS AND NORMAL BONE MARROW

| Residual clonogenic ability (%)* | | |
|---|---|---|
| Primary tumors | MCF-7 cells | Bone Marrow |
| 35.6 ± 41.2 (a) | 11.7 ± 4.8 | 104.7 ± 17.4 |
| (n = 4) | (n = 5) | (n = 7) |

*The percentages of colonies are referenced to controls obtained by incubating the different cell types in the presence of C' alone. n = ) number of different experiments.
(a) Mean ± SD.

TABLE 9

BIODISTRIBUTION OF $^{125}$I FC-5.01 AND UPC 10, 8 DAYS POSTADMINISTRATION.

| MAb | Tissue | Tumor/tissue cpm/gr tumor/ cpm/gr tissue (ml blood) | injected dose/gr tissue (% injected dose/gr) |
|---|---|---|---|
| FC-5.01 | tumor | 1.0 | 1.5 |
| | blood | 1.53 (cpm/ml) | 0.93 |
| | liver | 4.7 | 0.31 |
| | spleen | 2.07 | 0.72 |
| | lung | 3.84 | 0.39 |
| | kidney | 4.63 | 0.32 |
| | skin | 3.5 | 0.43 |
| | bone | 3.9 | 0.39 |

TABLE 9-continued

BIODISTRIBUTION OF $^{125}$I FC-5.01 AND UPC 10, 8 DAYS POSTADMINISTRATION.

| MAb | Tissue | Tumor/tissue cpm/gr tumor/ cpm/gr tissue (ml blood) | injected dose/gr tissue (% injected dose/gr) |
|---|---|---|---|
|  | tumor | 1.0 | 0.78 |
|  | blood | 0.45 (cpm/ml) | 1.58 |
|  | live | 1.34 | 0.58 |
| UPC 10 | spleen | 0.6 | 1.3 |
|  | lung | 0.94 | 1.11 |
|  | kidney | 1.18 | 0.66 |
|  | skin | 0.88 | 0.88 |
|  | bone | 1.25 | 0.63 |

For each labelled anitbody, two mice were sacrified 8 days after i.p. injection. The results are the average of 4 tumors (2 tumors per mouse).

TABLE 10

BIODISTRIBUTION OF $^{125}$I- FC-5.01 AND UPC 10 F(ab')2 FRAGMENTS

| MAb | Tissue | 12 | 24 | 36 (hr) | 48 | 72 |
|---|---|---|---|---|---|---|
|  | blood | 6.4 (a) | 1.05 | 2.6 | 4.15 | 3.2 |
|  | liver | 1.54 | 2.9 | 3.69 | 5.25 | 6.45 |
|  | spleen | 1.8 | 3.25 | 4.0 | 7.3 | 4.8 |
| 5.01 | lung | 1.73 | 3.2 | 3.2 | 5.45 | 5.6 |
|  | kidney | 0.76 | 1.31 | 0.64 | 1.7 | 2.2 |
|  | skin | 1.97 | 1.0 | 2.63 | 5.25 | 5.8 |
|  | bone | 4.2 | 3.7 | 3.2 | 11.7 | 6.9 |
|  | brain | 20.1 | 30.2 | 26.3 | 93.2 | 55.9 |
|  | blood | 0.4 | 0.54 | 0.2 | 0.67 | ND |
|  | liver | 1.6 | 1.6 | 1.9 | 2.4 | ND |
|  | spleen | 1.55 | 1.63 | 1.5 | 1.97 | ND |
| UPC10 | lung | 0.86 | 1.74 | 1.3 | 1.96 | ND |
|  | kidney | 0.19 | 0.25 | 0.16 | 0.16 | ND |
|  | skin | 1.3 | 0.99 | 0.96 | 1.25 | ND |
|  | bone | 1.8 | 2.3 | 0.99 | 1.33 | ND |
|  | brain | 12.3 | 10.3 | 7.6 | 5.7 | ND |

(a) Tumor:normal tissue ratio in cpm/gr

For each labelled antibody, two mice were sacrified 8 days after i.p. injection. The results are the average of 4 tumors (2 tumors per mouse).

TABLE 11

BIODISTRIBUTION OF $^{125}$I FC-5.01 AND UPC10 F(ab')2 FRAGMENTS

| MAb | Tissue | 12 | 24 | 36 (hr) | 48 | 72 |
|---|---|---|---|---|---|---|
|  | tumor | 0.6 (a) | 0.2 | 0.07 | 0.17 | 0.11 |
|  | liver | 0.4 | 0.08 | 0.02 | 0.03 | 0.02 |
|  | lung | 0.15 | 0.08 | 0.02 | 0.03 | 0.02 |
| 5.01 | spleen | 0.3 | 0.08 | 0.02 | 0.02 | 0.02 |
|  | kidney | 0.76 | 0.18 | 0.11 | 0.13 | 0.05 |
|  | skin | 0.3 | 0.25 | 0.03 | 0.03 | 0.02 |
|  | bone | 0.03 | 0.01 | 0.00 | 0.00 | 0.00 |
|  | brain | 0.14 | 0.07 | 0.02 | 0.02 | 0.01 |
|  | blood | 0.09 | 0.23 | 0.03 | 0.05 | 0.04 |
|  | tumor | 0.21 | 0.12 | 0.05 | 0.04 | ND |
|  | liver | 0.13 | 0.07 | 0.02 | 0.02 | ND |
|  | spleen | 0.2 | 0.07 | 0.04 | 0.02 | ND |
| UPC10 | lung | 0.14 | 0.07 | 0.03 | 0.02 | ND |
|  | kidney | 1.10 | 0.48 | 0.29 | 0.23 | ND |
|  | skin | 0.16 | 0.12 | 0.05 | 0.03 | ND |
|  | brain | 0.02 | 0.01 | 0.01 | 0.01 | ND |
|  | bone | 0.11 | 0.05 | 0.05 | 0.03 | ND |
|  | blood | 0.55 | 0.22 | 0.23 | 0.06 | ND |

(a): percentage of injected dose per gram.
ND: non determined

For each labelled antibody, two mice were sacrified 8 days after i.p. injection. The results are the average of 4 (2 tumors per mouse).

We claim:

1. A monoclonal antibody comprising a V region heavy chain having the amino acid sequence of SEQ. ID. NO. 7 and a V region light chain having the amino acid sequence of SEQ. ID. NO. 8.

2. A monoclonal antibody denominated FC-2.15 produced by the hybridoma cell line accorded deposit number 1-1875 as deposited with the Collection Nationale de Cultures de Microorganisms, Institute Pasteur.

3. A monoclonal antibody denominated FC-5.01 produced by the hybridoma cell line accorded deposit number 1-1876 as deposited with the Collection Nationale de Cultures de Microorganisms, Institute Pasteur.

4. A cell line producing the monoclonal antibody of claim 2.

5. A cell line producing the monoclonal antibody of claim 3.

6. A method comprising administering the antibody of claim 2 to an individual.

7. A method comprising administering the antibody of claim 3 an individual.

* * * * *

UNITED STATES PATENT AND TRADEMARK OFFICE
CERTIFICATE OF CORRECTION

PATENT NO. : 5,753,229
DATED : May 19, 1998
INVENTOR(S) : Jose MORDOH et al.

It is certified that error appears in the above-indentified patent and that said Letters Patent is hereby corrected as shown below:

In Figure 13A, change the three letter code for amino acid 51 from "Asp" to -- Asn --.

In Figure 13B, change the three letter code for amino acid 37 from "Gln" to -- Glu --.

Signed and Sealed this

Fifth Day of October, 1999

Q. TODD DICKINSON

*Attest:*

*Attesting Officer*                    Acting Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( v i i ) IMMEDIATE SOURCE:
      ( B ) CLONE: CHMu ( x i ) SEQUENCE DESCRIPTION: SEQ ID NO:1:

CATTGGGAAG GACTGACTC                                                                                          19

( 2 ) INFORMATION FOR SEQ ID NO:2:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: YES ( v i i ) IMMEDIATE SOURCE:
          ( B ) CLONE: CK2

( x i ) SEQUENCE DESCRIPTION: SEQ ID NO:2:

TGGATACAGT TGGTGCAGC                                                                                          19

( 2 ) INFORMATION FOR SEQ ID NO:3:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
          ( B ) CLONE: VHB ( x i ) SEQUENCE DESCRIPTION: SEQ ID NO:3:

AGG Y RCARCT GCAGSAGTCW GG                                                                                    22

( 2 ) INFORMATION FOR SEQ ID NO:4:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
          ( B ) CLONE: VKB-2

( x i ) SEQUENCE DESCRIPTION: SEQ ID NO:4:

GATATTGTGA TGACCCAGTC TCCA                                                                                    24

( 2 ) INFORMATION FOR SEQ ID NO:5:

( i ) SEQUENCE CHARACTERISTICS:
          ( A ) LENGTH: 371 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
　　( B ) CLONE: DNA - V region of heavy chain ( x i ) SEQUENCE DESCRIPTION: SEQ ID NO:5:

| AGGTGAAGCT | GCAGGAGTCT | GGAGGTGGCC | TCGTGCAGCC | TGGAGGATCC | CTGAAACTCT | 60 |
| CCTGTGCAGC | CTCAGGATTC | GATTTTAGTA | GATACTGGAT | CAGTTGGCTC | CGGCAGGCTC | 120 |
| CAGGGAAAGG | GCTAGAATGG | ATTGGAGAAA | TTAATCCAGA | TACCAGTACC | ATAAACTATA | 180 |
| CGCCATCTCT | AAAGGATAAA | TTCATCATCT | CCAGAGACAA | CGCCAAAAAT | ACGCTGTACC | 240 |
| TGCAAATGAG | CAAAGTGAGA | TCTGAGGACA | CAGCCCTTTA | TTACTGTGCA | AGAGAGACTG | 300 |
| GGACGCCTTT | TGACTACTGG | GGCCAAGGCA | CCACTCTCAC | AGTCTCCTCA | GAGAGTCAGT | 360 |
| CCTTCCCAAA | T | | | | | 371 |

( 2 ) INFORMATION FOR SEQ ID NO:6:

( i ) SEQUENCE CHARACTERISTICS:
　　　　( A ) LENGTH: 349 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
　　　　( B ) CLONE: DNA - V region of light chain ( x i ) SEQUENCE DESCRIPTION: SEQ ID NO:6:

| GATATTGTGA | TGACCCAGTC | TCCAGCATCC | CTGTCCGTGG | CTACAGGAGA | AAAAGTCACT | 60 |
| ATCAGATGCA | TAACCAGCAC | TGATATTGAT | GATGATATGA | ACTGGTACCA | GCAGAAGCCA | 120 |
| GGGGAACCTC | CTAAGCTCCT | TATTTCAGAA | GGCAATACTC | TTCGTCCTGG | AGTCCCATCC | 180 |
| CGATTCTCCA | GCAGTGGCTA | TGGCACAGAT | TTTGTTTTTA | CAATTGAAAA | CACGCACTCA | 240 |
| GAAGATGTTG | CAGATTACTA | CTGTTTGCAA | AGTGATAACA | TGCCATTCAC | GTTCGGCTCG | 300 |
| GGGACAAAGT | TGGAAATAAA | ACGGGCTGAT | GCTGCACCAA | CTGTATCCA | | 349 |

( 2 ) INFORMATION FOR SEQ ID NO:7:

( i ) SEQUENCE CHARACTERISTICS:
　　　　( A ) LENGTH: 122 amino acids
　　　　( B ) TYPE: amino acid
　　　　( C ) STRANDEDNESS: single
　　　　( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
　　　　( B ) CLONE: V region of heavy chain ( x i ) SEQUENCE DESCRIPTION: SEQ ID NO:7:

Val Lys Leu Gln Glu Ser Gly Gly Gly Leu Val Gln Pro Gly Gly Ser
  1               5                  10                  15

-continued

| | | | | | | | | | | | | | | | |
|---|---|---|---|---|---|---|---|---|---|---|---|---|---|---|---|
| Leu | Lys | Leu 20 | Ser | Cys | Ala | Ala | Ser 25 | Gly | Phe | Asp | Phe | Ser 30 | Arg | Tyr | Trp |
| Met | Ser | Tyr 35 | Val | Arg | Gln | Ala | Pro 40 | Gly | Lys | Gly | Leu | Glu 45 | Trp | Ile | Gly |
| Glu | Ile 50 | Asp | Pro | Asp | Ser | Ser 55 | Thr | Ile | Asn | Tyr | Thr 60 | Pro | Ser | Leu | Lys |
| Asp 65 | Lys | Phe | Ile | Ile | Ser 70 | Arg | Asp | Asn | Ala | Lys 75 | Asn | Thr | Leu | Tyr | Leu 80 |
| Gln | Met | Ser | Lys | Val 85 | Arg | Ser | Glu | Asp | Thr 90 | Ala | Leu | Tyr | Tyr | Cys 95 | Ala |
| Arg | Glu | Thr | Gly 100 | Thr | Pro | Phe | Asp | Tyr 105 | Trp | Gly | Gln | Gly | Thr 110 | Thr | Leu |
| Thr | Val | Ser 115 | Ser | Glu | Ser | Gln | Ser 120 | Phe | Pro | | | | | | |

( 2 ) INFORMATION FOR SEQ ID NO:8:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i i ) IMMEDIATE SOURCE:
        ( B ) CLONE: V region of light chain ( x i ) SEQUENCE DESCRIPTION: SEQ ID NO:8:

| | | | | | | | | | | | | | | | |
|---|---|---|---|---|---|---|---|---|---|---|---|---|---|---|---|
| Asp 1 | Ile | Val | Met | Thr 5 | Gln | Ser | Pro | Ala | Ser 10 | Leu | Ser | Val | Ala | Thr 15 | Gly |
| Glu | Lys | Val | Thr 20 | Ile | Arg | Cys | Ile | Thr 25 | Ser | Thr | Asp | Ile | Asp 30 | Asp | Asp |
| Met | Asn | Trp 35 | Tyr | Glu | Gln | Lys | Pro 40 | Gly | Glu | Pro | Pro | Lys 45 | Leu | Leu | Ile |
| Ser | Glu 50 | Gly | Asn | Thr | Leu | Arg 55 | Pro | Gly | Val | Pro | Ser 60 | Pro | Phe | Ser | Ser |
| Ser 65 | Gly | Tyr | Gly | Thr | Asp 70 | Phe | Val | Phe | Thr | Ile 75 | Glu | Asn | Thr | His | Ser 80 |
| Glu | Asp | Val | Ala | Asp 85 | Tyr | Tyr | Cys | Leu | Gln 90 | Ser | Asp | Asn | Met | Pro 95 | Phe |
| Thr | Phe | Gly | Ser 100 | Gly | Thr | Lys | Leu | Glu 105 | Ile | Lys | Pro | Ala | Asp 110 | Ala | Ala |
| Pro | Thr | Val 115 | Ser | | | | | | | | | | | | |